Figure 1:
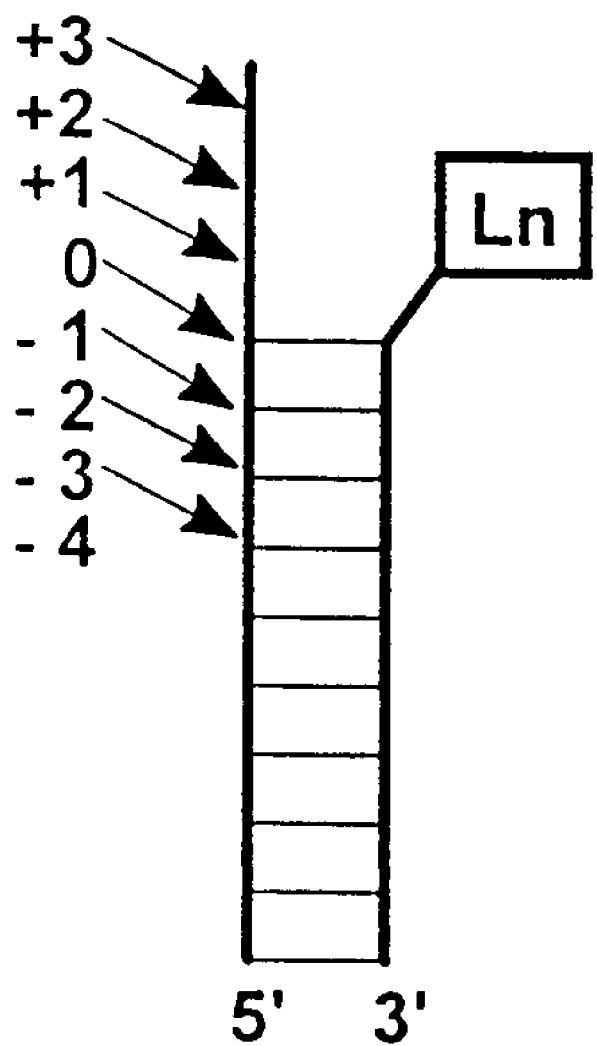

United States Patent [19]
Häner et al.

[11] Patent Number: 5,925,744
[45] Date of Patent: Jul. 20, 1999

[54] FUNCTIONAL TERPYRIDINE-METAL COMPLEXES, A PROCESS FOR THE PREPARATION THEREOF AND OLIGONUCLEOTIDE CONJUGATES WITH TERPYRIDINE-METAL COMPLEXES

[75] Inventors: Robert Häner, Fehren; Jonathan Hall, Bern, both of Switzerland; Dieter Hüsken, Freiburg; Uwe Pieles, Schliengen, both of Germany; Heinz Moser, Southwater, United Kingdom

[73] Assignee: Novartis Finance Corporation, New York, N.Y.

[21] Appl. No.: 08/793,530

[22] PCT Filed: Aug. 30, 1995

[86] PCT No.: PCT/EP95/03409

§ 371 Date: Jul. 28, 1997

§ 102(e) Date: Jul. 28, 1997

[87] PCT Pub. No.: WO96/07668

PCT Pub. Date: Mar. 14, 1996

[30] Foreign Application Priority Data

Sep. 2, 1994 [CH] Switzerland .............. 2693/94

[51] Int. Cl.$^6$ .............. C07F 5/00; A61K 51/00; C07D 213/22; C07C 69/96
[52] U.S. Cl. .............. 534/15; 534/10; 534/16; 424/1.65; 424/1.69; 424/9.363; 424/9.362; 546/256; 546/257; 558/260
[58] Field of Search .............. 534/10, 11, 12, 534/13, 14, 15, 16; 424/1.65, 9.363, 9.361, 9.362, 1.69; 546/256, 257; 558/260

[56] References Cited

U.S. PATENT DOCUMENTS 5,559,207  9/1996  Sessler et al. .............. 530/300
5,760,191  6/1998  Snow et al. .............. 534/10

FOREIGN PATENT DOCUMENTS 0266099  5/1988  European Pat. Off. .
8707300  12/1987  WIPO .
8908146  9/1989  WIPO .
9429316  12/1994  WIPO .

OTHER PUBLICATIONS

Biochemistry, vol. 29, No. 10, 1990, pp. 2515–2523, Linda S. Behlen, et al.
J. Am. Chem. Soc., vol. 112, No. 7, 1990, Christine S. Chow, et al., pp. 2839–2841.
Eur. J. Biochem., vol. 182, pp. 445–450, 1989 Jerzy Ciesiolka et al.
Polyhedron 7 (1988) E. C. Constable et al., pp. 2531–2536.
Inorganic Chemistry, vol. 32, No. 26, 1993, pp. 5899–5900, Nobuhiro Hayashi, et al.
Biochemistry, vol. 27, No. 15, 1988, pp. 5771–5777 W.J. Kryzosiak, et al.
J. Am. Chem. Soc., vol. 116, No. 16, Aug. 10, 1994, pp. 7439–7440, D. Magda, et al.
Nucleic Acids Research, vol. 17, No. 13, 1989 pp. 5361–5375, George J. Murakawa, et al.
Chemical Reviews, vol. 90, No. 4, Jun. 1990, pp. 543–584, Eugen Uhlmann, et al.
Science, vol. 254, 1991, pp. 1497–1500, Peter E. Nielsen, et al.
Chemistry and Biology, vol. 1, No. 3, 1994, pp. 185–190, Jonathan Hall, et al.
Polyhedron, vol. 1, No. 3, 1982, pp. 303–306, Edwin C. Constable, et al.

*Primary Examiner*—Jose' G. Dees
*Assistant Examiner*—Michael G. Hartley
*Attorney, Agent, or Firm*—Myra H. McCormack

[57] ABSTRACT

The present invention relates to cyclic terpyridine-lanthanide complexes having 8 nitrogen atoms and 10 carbon atoms in the macrocycle and containing a functional group in the terpyridine moiety. The invention also relates to a process for the preparation of cyclic terpyridine-lanthanide complexes through the condensation of terpyridine hydrazines with pyridine-2,6-dialdehydes or -ketones. The compounds can be complexed with oligonculeotides and are useful in the sequence-specific cleavage of RNA.

44 Claims, 2 Drawing Sheets

CG-1352  5' r (CUA  GCC  GAC  UGC  CGA  UCU  CGC  UGA  CUG  AC)

FUNCTIONAL TERPYRIDINE-METAL COMPLEXES, A PROCESS FOR THE PREPARATION THEREOF AND OLIGONUCLEOTIDE CONJUGATES WITH TERPYRIDINE-METAL COMPLEXES

This is a 371 PCT/EP95/03409 filed Aug. 30, 1995.

The present invention relates to cyclic terpyridine-lanthanide complexes having 8 nitrogen atoms and 10 carbon atoms in the macrocycle and containing a functional group in the terpyridine moiety, to a process for the preparation thereof by condensation of terpyridine hydrazines with pyridine-2,6-dialdehydes or -ketones, to associates of those complexes with oligonucleotides and to methods for the sequence-specific cleavage of RNA using those associates.

The hydrolytic cleavage of RNA under the catalytic action of metal ions has already been known for a long time. The cleavage takes place basically in unpaired regions of the RNA known as "loops". W. J. Krzyzosiak et al., Biochemistry 27:5771–5777 (1988) propose the use of lead diacetate for that purpose. G. J. Murakawa et al., Nucleic Acid Research 17:5361–5375 (1989) describe the use of copper complexes of 1,10-phenanthroline. J. Ciesiolka et al., Eur. J. Biochem. 182:445–450 (1989) disclose europium trichloride for the same purpose for cleaving tRNA$^{Phe}$. In J. Am. Chem. Soc., Volume 112, pages 2839 to 2841 (1990), C. S. Chow et al. use for the same RNA ruthenium and rhodium complexes with phenanthroline ligands. In Biochemistry, Volume 29, pages 2515 to 2523, L. S. Behlen et. al. mention tRNA$^{Phe}$ mutants with lead diacetate. In addition, N. Hayashi et al. describe in Inorg. Chem., Volume 32, pages 5899 to 5900 (1993) that lanthanide metal complexes are also suitable for the cleavage of tRNA.

It has been described by D. Magda et al. in J. Am. Chem. Soc., Volume 116, 7439 to 7440 (1994) that conjugates of europium(III)-texaphyrine and oligonucleotides with DNA building blocks are capable of cleaving a target RNA, a cleavage of only about 30% being observed in the region of the texaphyrine complex in the RNA/oligonucleotide complex. A further disadvantage of those texaphyrine complexes is that in addition hydroxypropyl must be bonded in the ligand so as to ensure sufficient solubility. Furthermore, the imine groups of the ligand are susceptible to hydrolysis, so that the effectiveness in an aqueous environment declines relatively quickly; that is to say the residence time is too low for therapeutic applications. In addition, hydrolysis of the ligand liberates the metal and this can bring about serious toxicity problems and nonspecific cleavage of the RNA. They are also weak Lewis acids because a charge on the Eu cation is neutralised by a ligand and therefore a complex having two charges is present. In addition, the described complexes can be obtained only by procedures that are expensive in terms of synthesis.

It is known that in cells the formation of physiologically harmful polypeptides is brought about by the gene-controlled formation of mRNA. In order to combat or prevent diseases it is therefore desirable to have agents that impede the action of the mRNA. In particular, the mRNA should be destroyed by irreversible cleavage at a defined site and the information content should therefore be lost. It is also desirable by a sequence-specific cleavage of RNA chains to provide fragments that can be used for the more rapid synthesis of oligonucleotides in the "antisense field" for diagnostic purposes (biosensors) or for the treatment of diseases by affecting metabolic processes in the cell.

It has now been found that oligonucleotides the sequence of which is complementary to a target RNA and to which a terpyridine-lanthanide complex is bonded are highly effective and it is possible to achieve sequence-specific cleavages in a target RNA.

The present invention relates to compounds of formula I

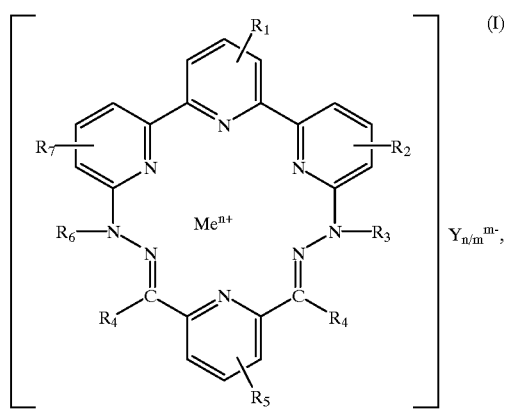

wherein
$R_1$ is H or a substituent and $R_5$ is a monovalent functional group or $R_1$ is a monovalent functional group and $R_5$ is H or a substituent, the functional group being bonded to the pyridine ring directly or via a group Z and the group Z being a radical selected from the group consisting of $C_1$–$C_{20}$alkylene, $C_2$–$C_{12}$alkenylene, $C_2$–$C_{12}$alkynylene, $C_5$–$C_8$cycloalkylene, $C_6$–$C_{12}$arylene and $C_7$–$C_{12}$aralkylene, which radical is uninterrupted or interrupted by —O—, —S—, —NR$_{12}$—, —C(O)—O— or by —C(O)—NR$_{12}$—, $R_2$ and $R_7$ are each independently of the other H, $C_1$–$C_4$alkyl, $C_1$–$C_4$alkoxy, $C_7$–$C_{12}$aralkyl, $C_6$–$C_{16}$aryl or halogen, $R_3$ and $R_6$ are each independently of the other H, $C_1$–$C_4$alkyl, $C_7$–$C_{12}$aralkyl or $C_6$–$C_{16}$aryl, $R_4$ is H, $C_1$–$C_{20}$alkyl, $C_5$–$C_8$cycloalkyl, $C_6$–$C_{12}$aryl or $C_7$–$C_{12}$aralkyl, $R_{12}$ is H or $C_1$–$C_6$alkyl, Me is a lanthanide metal or yttrium, Y is an anion of an acid, n is the number 2 or 3, and m is the number 1, 2 or 3, the radicals alkyl, cycloalkyl, aralkyl, aryl and the group Z being unsubstituted or substituted by $C_1$–$C_4$alkoxy, F, Cl, Br, —CN, $C_1$–$C_4$alkyl or by —NO$_2$.

$R_1$ and $R_5$ as substituents are preferably $C_1$–$C_4$alkyl, $C_1$–$C_4$alkoxy, $C_7$–$C_{12}$aralkyl or $C_6$–$C_{16}$-aryl, $C_4$–$C_{12}$heteroaryl having O, S, N as hetero atoms, $C_1$–$C_4$alkylthio, di($C_1$–$C_4$alkyl)amino, halide, sulfonamide and carboxamide.

$R_1$ and $R_5$ are preferably bonded in the p-position to the nitrogen atom of the pyridine ring.

$R_2$, $R_3$, $R_6$ and $R_7$ as alkyl are preferably methyl or ethyl, as alkoxy preferably methoxy or ethoxy, as aralkyl preferably benzylene or phenylethylene, and as aryl preferably naphthyl and especially benzyl. In a preferred embodiment, $R_2$ and $R_7$ are H and $R_3$ and $R_6$ are alkyl. Especially, $R_2$ and $R_7$ are H and $R_3$ and $R_6$ are $C_1$–$C_4$alkyl and more especially methyl. $R_2$, $R_3$, $R_6$ and $R_7$ may also be $C_4$–$C_{12}$heteroaryl having O, S, N as hetero atoms. Examples are pyridyl, thiazolyl, imidazolyl, oxazolyl, furanosyl, pyrrolyl and thiophenyl. They may also be $C_1$–$C_4$alkylthio, halide, di($C_1$–$C_4$alkyl)amino, sulfonamide and carboxamide.

$R_4$ as alkyl contains preferably from 1 to 12, especially from 1 to 8 and more especially from 1 to 4, carbon atoms. Some examples of alkyl are methyl, ethyl and the isomers of propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl.

$R_4$ as cycloalkyl contains preferably 5 or 6 ring carbon atoms. Some examples of cycloalkyl are cyclopropyl, cyclobutyl, cyclopentyl, cyclohexyl, cyclopentyl and cyclooctyl.

$R_4$ as aryl is preferably naphthyl and especially phenyl. When $R_4$ is aralkyl, it is preferably benzyl or phenylethyl.

A preferred subgroup for $R_4$ is H, $C_1$–$C_4$alkyl, especially methyl, and phenyl or benzyl.

$R_1$ and $R_5$ as alkyl are preferably methyl or ethyl, as alkoxy preferably methoxy or ethoxy, as aryl preferably naphthyl or phenyl, and as aralkyl preferably phenyl or phenylethyl. Preferably $R_1$ and $R_5$ are H, methyl, ethyl, methoxy or ethoxy.

Within the scope of the present invention, the monovalent functional group is preferably selected from the group consisting of —$OR_{10}$, —$SR_{10}$, —NCO, —NCS, —$NHR_{11}$, —C(O)$OR_{11}$, —C(O)SH, —C(O)$NHR_{11}$, —C(O)Cl, —C(S)$SR_{11}$, —C(S)$NHR_{11}$, —C(S)$OR_{11}$, —$SO_3R_{11}$, —$SO_2NHR_{11}$, —$SO_2$Cl, —P(O)(OH)$_2$, —P(O)(OH)—$NHR_{11}$, —P(S)(SH)$_2$, —P(S)(SH)—$NHR_{11}$, —P(S)(OH)$_2$, —P(S)(OH)—$NHR_{11}$, —P(O)(SH)$_2$, —P(O)(SH)—$NHR_{11}$, —P(O)(OH)H, —P(O)($NHR_{11}$)H, —P(S)(SH)H, —P(S)($NHR_{11}$)H, —P(S)(OH)H and —P(O)(SH)H, with $R_{10}$ being H, —C(O)$NH_2$, —C(S)$NH_2$, —$C_1$–$C_6$alkyl, —$C_xH_{2x}$—$NH_2$, —$C_xH_{2x}$—SH or —($C_xH_{2x}$O)$_y$—H and $R_{11}$ being H, —$C_1$–$C_6$alkyl, —$C_xH_{2x}$—$NH_2$, —$C_xH_{2x}$—SH or —($C_xH_{2x}$O)$_y$—H and x being a number from 2 to 6 and y being a number from 1 to 20. The functional group is especially selected from the group consisting of —$OR_{10}$, —$SR_{10}$, —NCO, —NCS, —$NHR_{11}$, —C(O)$OR_{11}$ and —P(O)(OH)$_2$, more especially selected from the group consisting of —NCS, —C(O)$OR_{11}$ and —P(O)(OH)$_2$.

A preferred subgroup of compounds of formula I comprises those wherein $R_2$ and $R_7$ are H, $R_3$ and $R_6$ are $C_1$–$C_4$alkyl, $R_4$ is H, $C_1$–$C_4$alkyl, phenyl or benzyl, $R_1$ is a monovalent functional group bonded via $C_1$–$C_3$alkylene, $C_3$alkynylene, phenylene or $C_7$aralkylene, preferably via $C_2$–$C_3$alkylene or phenylene, and $R_5$ is H, methyl or methoxy, or $R_5$ is a monovalent functional group bonded via $C_1$–$C_3$alkylene, $C_3$alkynylene, phenylene or $C_7$aralkylene, preferably via $C_2$–$C_3$alkylene or phenylene, and $R_1$ is H, methyl or methoxy.

Within the scope of the present invention, a lanthanide metal is to be understood as being any lanthanide, that is to say lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu). Preference is given to La, Ce, Nd, Eu and Gd, especially to La and Eu, and more especially to Eu.

Suitable anions for the complex salts can be selected, for example, from the following group: halide (for example Cl$^-$, Br$^-$ and I$^-$), the anion of an oxyacid, $BF_4^-$, $PF_6^-$, $SiF_6^-$ and $AsF_6^-$.

The anions of oxyacids may be, for example: sulfate, phosphate, perchlorate, perbromate, periodate, antimonate, arsenate, nitrate, carbonate, the anion of a $C_1$–$C_8$carboxylic acid, for example formate, acetate, propionate, butyrate, benzoate, phenylacetate, mono-, di- or tri- chloro- or -fluoro-acetate, sulfonates, for example methylsulfonate, ethylsulfonate, propylsulfonate, butylsulfonate, trifluoromethylsulfonate (triflate), unsubstituted or $C_1$–$C_4$alkyl-, $C_1$–$C_4$alkoxy- or halo-substituted, especially fluoro-, chloro- or bromo-substituted, phenylsulfonate or benzylsulfonate, for example tosylate, mesylate, brosylate, p-methoxy- or ethoxy-phenylsulfonate, pentafluorophenylsulfonate or 2,4,6-triisopropylsulfonate, and phosphonates, for example methylphosphonate, ethylphosphonate, propylphosphonate, butylphosphonate, phenylphosphonate, p-methylphenylphosphonate and benzyl-phosphonate. Suitable anions are also tartrate, citrate and lactate. Preferred anions within the scope of the present invention are F$^-$, Cl$^-$, Br$^-$, I$^-$, $PF_6^-$, $SbF_6^-$, $BF_4^-$, $B(Ph)_4^-$, acetate, $NO_3^-$, sulfate and phosphate; especially preferred anions are Cl$^-$, acetate and $NO_3^-$.

The preferences and explanations, especially of the substituents, given above for the compound of formula (I) apply correspondingly also to the compound of formula (V) described below.

The present invention relates also to compounds of formula V

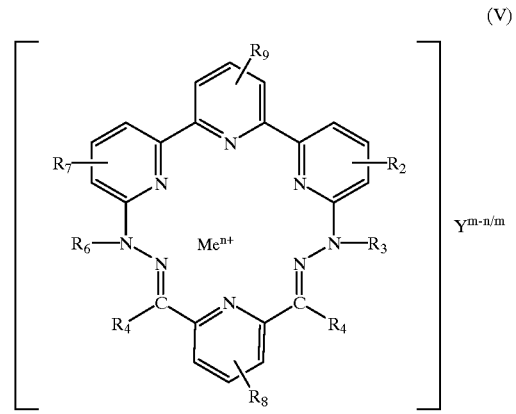

(V)

wherein $R_2$ and $R_7$ are each independently of the other H, $C_1$–$C_4$alkyl, $C_1$–$C_4$alkoxy, $C_7$–$C_{12}$aralkyl, $C_6$–$C_{16}$aryl or halogen, $R_3$ and $R_6$ are each independently of the other H, $C_1$–$C_4$alkyl, $C_7$–$C_{12}$aralkyl or $C_6$–$C_{16}$aryl, $R_4$ is H, $C_1$–$C_{20}$alkyl, $C_5$–$C_8$cycloalkyl, $C_6$–$C_{12}$aryl or $C_7$–$C_{12}$aralkyl, the radicals alkyl, cycloalkyl, aralkyl and aryl being unsubstituted or substituted by $C_1$–$C_4$alkoxy, F, Cl, Br, —CN, $C_1$–$C_4$alkyl or by —$NO_2$, Me is a lanthanide metal or yttrium, Y is an anion of an acid, n is the number 2 or 3, and m is the number 1, 2 or 3, $R_9$ is a radical of formula VI

(VI), and $R_8$ is H or a substituent or $R_9$ is H or a substituent and $R_8$ is a radical of formula VI, p, q and r are each independently of the others 0 or 1, X and X' are each independently of the other a radical selected from the group consisting of $C_1$–$C_{20}$alkylene, $C_2$–$C_{12}$alkenylene, $C_2$–$C_{12}$alkynylene, —$(C_xH_{2x}O)_y$—, wherein x is a number from 2 to 6 and y is a number from 1 to 20, $C_5$–$C_8$cycloalkylene, $C_6$–$C_{12}$arylene and $C_7$–$C_{12}$-aralkylene, which radical is unsubstituted or substituted by $C_1$–$C_4$alkoxy, F, Cl, Br, —CN, $C_1$–$C_4$alkyl or by —$NO_2$, A and A' are each independently of the other —O—, —S—, —S—S—, —$NR_{12}$—CO—$NR_{12}$—, —$NR_{12}$CS—$NR_{12}$—, —$NR_{12}$—, —$NR_{12}$—C(O)—O—, —C(O)O—, —C(O)S—, —C(O)$NR_{12}$—, —C(S)S—, —C(S)O—, —C(S)$NR_{12}$—, —$SO_2NR_{12}$—, —$SO_2$—, —P(O)(OH)O—, —P(S)(SH)S—, —P(S)(SH)O—, —P(S)(OH)O—, —P(O)(SH)S—, —P(O)(OH)S—, —P(O)(SH)O—, —P(O)(OH)—$NR_{12}$—, —P(S)(SH)—$NR_{12}$—, —P(S)(OH)—$NR_{12}$—, —P(O)(SH)—$NR_{12}$—, —HP(O)O—, —HP(S)S—, —HP(O)$NR_{12}$— or —HP(S)$NR_{12}$—, with $R_{12}$ being H or $C_1$–$C_6$alkyl; and "oligo" denotes a natural, modified or synthetic sequence of natural, modified or synthetic deoxynucleosides or peptide nucleic acid building blocks that is bonded via a nucleic base, an internucleotidic bridge or a sugar and the internal region of which is complementary, preferably completely complementary, to a target RNA.

Here q is preferably 1.

The definitions and preferences given above for $R_5$ and $R_1$ apply analogously to $R_8$ and $R_9$ as substituents.

Target RNA within the scope of the present invention means that a RNA sequence must be present in the target. Accordingly, polyribonucleic acids (RNA) may be present. They are preferably m-RNA (messenger RNA), pre-m-RNA (precursor m-RNA), t-RNA (transfer RNA), sn-RNA (small nuclear RNA), r-RNA (ribosomal RNA) and viral RNA. However, it is also possible for mixed sequences of RNA and polydeoxyribonucleic acids (DNA) to be present, for example the chimeras RNA-DNA (Okazaki fragment). The RNA has a sufficient number of building blocks for a complex (double strand) to be formed with the oligonucleotide.

Within the scope of the invention, the internal region of a sequence is to be understood as meaning that, for example, up to 5, preferably up to 3 and especially 1 or 2, of the outer nucleotide building blocks of the sequence need not be complementary to the target RNA. This may be advantageous insofar as the terpyridine-lanthanide complex bonded at the end of the sequence may be more mobile and therefore more efficient.

The oligonucleotide may be composed partly or completely of natural DNA building blocks complementary to the target RNA or it may be composed completely of unnatural synthetic nucleotides that are likewise complementary to the target RNA, "partly" meaning that in the oligonucleotide sequence natural DNA building blocks complementary to the target RNA have been replaced by unnatural synthetic nucleotides that are likewise complementary. Synthetic building blocks include the modifications of natural building blocks in the nucleic base, in the furanose ring and/or in the bridge groups of the oligonucleotides. Synthetic building blocks are generally used in order to strengthen the complex bond in duplex structures and/or to increase the stability of the oligonucleotides with respect to the degradation caused by, for example, nucleases. A large number of modified nucleosides have become known in the field of "antisense technology" for the synthesis or modification of complementary oligonucleotides and are therefore not described in detail here (see, for example, E. Uhlmann et al., Chemical Reviews, Volume 90, Number 4, pages 543 to 584 (1990)).

Suitable modifications are modifications in the nucleic base moiety (for example substitutions, omission of substituents), in the nucleotide bridge group (for example modification of the phosphoric acid ester group or the replacement thereof by other bridge groups) and in the furanose ring (for example substitutions at the 2'-hydroxyl group, replacement of the furanose oxygen atom, replacement of the furanose ring by mono- or bi-carbacyclic rings, replacement of the furanose ring by open-chain structures).

The selection and the order of the building blocks in the sequence of the oligonucleotide are determined by the required duplex formation with a target RNA. The nature and location of the linkage with the terpyridine-lanthanide complex can also affect the selection and the order of the building blocks.

The number of building blocks in the oligonucleotide is such that hybridisation with the target RNA takes place. The oligonucleotides may contain, for example, from 5 to 100, preferably from 5 to 50, especially from 8 to 30 and more especially from 10 to 25, building blocks. The regions that increase pair formation with the target RNA (pairing nucleotide building blocks) are arranged preferably in the middle sequence orders of the oligonucleotide, for example between the fourth-last building blocks, or the third-last building blocks, or the second-last building blocks or the last building blocks of the sequence. In the case of an oligonucleotide having, for example, 20 building blocks, pairing building blocks are located preferably in the region from the fourth to the seventeenth building block.

The oligonucleotides are preferably composed of nucleosides of the purine series and the pyrimidine series, especially of 2'-deoxy-2-aminoadenosine, 2'-deoxy-5-methylcytidine, 2'-deoxyadenosine, 2'-deoxycytidine, 2'-deoxyuridine, 2'-deoxyguanosine and 2'-thymidine. Special preference is given to 2'-deoxyadenosine (A), 2'-deoxycytidine (C), 2'-deoxyguanosine (G) and 2'-thymidine (T). Modified building blocks are derived preferably from natural nucleosides of the purine series and the pyrimidine series, especially from adenosine, cytidine, guanosine, 2-aminoadenosine, 5-methylcytosine, thymidine and the afore-mentioned deoxy derivatives. Nucleosides may also be 2'-modified ribonucleosides.

In an especially preferred embodiment of the invention, the oligonucleotide complementary to a target RNA is composed of natural deoxynucleosides, especially from the group 2'-deoxyadenosine (A), 2'-deoxycytidine (C), 2'-deoxyguanosine (G) and 2'-thymidine (T), or of complementary unnatural synthetic building blocks. Within the scope of the invention special preference is given to those modified nucleosides which increase the stability of the oligonucleotide with respect to nucleases.

The oligonucleotide may also comprise sequences of peptide nucleic acids (PNA), the terpyridine-lanthanide complex preferably being bonded to the nucleic base, the amino end or the carboxyl end. The same preferences apply to the structure of the PNA sequence as to the structure of the oligonucleotides. Examples of PNAs can be found in Science, Volume 254, pages 1497 to 1500.

The terpyridine-lanthanide complex is preferably bonded via a bridge group to N, S or O atoms in the 3'- or 5'-terminal groups in the oligonucleotide sequence. It may, however, also be bonded to C, N or O atoms of nucleic bases in or at the end of the sequence, to 2'-positions of the furanose ring, to O, S or N atoms in or at the end of the sequence or to O, S or N atoms of the nucleotide bridge group in the sequence. The nature of the bond depends upon the terpyridine-lanthanide complex and the nature of its functional groups.

A bridge group may be, for example, a modified functional group which in turn may be bonded directly or via a connecting group to the terpyridine-lanthanide complex and/or to the oligonucleotide. The bond to the oligonucleotide may be ionic and, preferably, covalent. The terpyridine-lanthanide complex may also be bonded to the 6'-carbon atom of a carbacyclic nucleotide analogue.

When X and X' are components of the bridge between terpyridine-lanthanide complex and oligonucleotide, $X_0$ or $X_0'$ may be a direct bond or $X_1$ or $X_1'$ may be a bivalent, open-chain or cyclic hydrocarbon group having from 1 to 22 carbon atoms and being uninterrupted or interrupted by radicals from the group —S—, —NR$_{12}$—, —C(O)—O— and —C(O)—NR$_{12}$—, or a polyoxaalkylene radical having from 1 to 12 oxaalkylene units and 2 or 3 carbon atoms in the alkylene. The hydrocarbon group may be, for example, linear or branched $C_1$–$C_{22}$alkylene, preferably $C_1$–$C_{18}$alkylene, especially $C_1$–$C_{12}$alkylene and more especially $C_1$–$C_8$alkyl; $C_3$–$C_8$cycloalkylene, preferably $C_5$- or $C_6$-cycloalkylene; $C_6$–$C_{12}$arylene or $C_7$–$C_{12}$aralkylene. Some examples of bivalent hydrocarbon groups are methylene, ethylene, 1,2- or 1,3-butylene, 1,2-, 1,3- or 1,4-butylene, 1,2-, 1,3-, 1,4- or 1,5-pentylene, 1,2-, 1,3-, 1,4-, 1,5- or 1,6-hexylene, 1,2-, 1,3-, 1,4-, 1,5-, 1,6- or 1,7-heptylene, 1,2-, 1,3-, 1,4-, 1,5-, 1,6-, 1,7- or 1,8-octylene, and the isomers of nonylene, decylene, undecylene, dodecylene, tridecylene, tetradecylene, pentadecylene, hexadecylene, heptadecylene, octadecylene, nonadecylene and eicosylene; cyclopentylene, cyclohexylene; naphthylene and especially phenylene; benzylene and phenylethylene. Some examples of polyoxaalkylenes are ethyleneoxy, bisethyleneoxy, trisethyleneoxy, tetraethyleneoxy and 1,2-propoxy. Special preference is given to bridge groups wherein X is $C_1$–$C_3$alkylene, $C_3$alkynylene, phenylene or $C_7$aralkylene, especially $C_2$–$C_3$alkylene or phenylene. Bridge groups in which X' is $C_1$–$C_{20}$alkylene, especially $C_1$–$C_{10}$alkylene, are also especially preferred.

The bivalent group A is preferably —NR$_{12}$—CS—NR$_{12}$— or —C(O)NR$_{12}$—, especially —NH—CS—NH— or —C(O)NH—.

Preferred compounds of formula V are those wherein A' is absent or is —P(O)(OH)O—.

Preferred compounds of formula V are those wherein $R_2$ and $R_7$ are each independently of the other H or $C_1$–$C_4$alkyl.

Advantageously, $R_3$ and $R_6$ are each independently of the other H or $C_1$–$C_4$alkyl.

In another preferred embodiment, $R_4$ is H or $C_1$–$C_{20}$alkyl.

The preferences relating to suitable lanthanides and anions have already been mentioned. They apply also to the compounds of formula V.

The present invention relates also to intermediates in the preparation of compounds of formula I. They are compounds of formula II

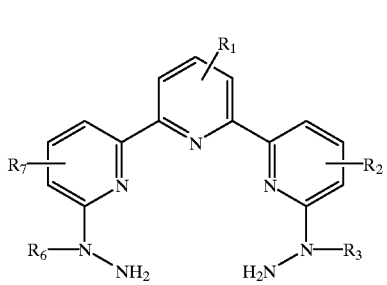

(II)

wherein $R_1$ is H, $C_1$–$C_4$alkyl, $C_1$–$C_4$alkoxy, $C_7$–$C_{12}$aralkyl or $C_6$–$C_{16}$aryl or a monovalent functional group, the functional group being bonded to the pyridine ring directly or via a group Z and the group Z being a radical selected from the group consisting of $C_1$–$C_{20}$alkylene, $C_2$–$C_{12}$-alkenylene, $C_2$–$C_{12}$alkynylene, $C_5$–$C_8$cycloalkylene, $C_6$–$C_{12}$arylene and $C_7$–$C_{12}$aralkylene, which radical is uninterrupted or interrupted by —O—, —S—, —NR$_{12}$—, —C(O)—O— or by —C(O)—NR$_{12}$—, $R_2$ and $R_7$ are each independently of the other H, $C_1$–$C_4$alkyl, $C_1$–$C_4$alkoxy, $C_7$–$C_{12}$aralkyl, $C_{6-16}$aryl or halogen, and $R_3$ and $R_6$ are each independently of the other H, $C_1$–$C_4$alkyl, $C_7$–$C_{12}$aralkyl or $C_6$–$C_{16}$aryl, $R_{12}$ is H or $C_1$–$C_6$alkyl, the radicals alkyl, cycloalkyl, aralkyl, aryl and the group Z being unsubstituted or substituted by $C_1$–$C_4$alkoxy, F, Cl, Br, —CN, $C_1$–$C_4$alkyl or by —NO$_2$.

Further intermediates in the preparation of compounds of formula I, to which the present invention also relates, are compounds of formula III

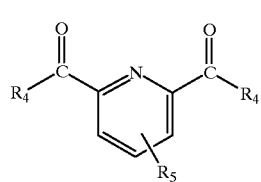

(III)

wherein $R_5$ is a monovalent functional group bonded to the pyridine ring via $C_2$–$C_{20}$alkylene, the functional group being selected from the group consisting of —C(O)—OR$_{12}$, —C(O)—NHR$_{12}$, —SO$_2$—R$_{12}$ and —SO$_2$—NHR$_{12}$, with R$_{12}$ being H or $C_1$–$C_6$alkyl, and $R_4$ is H or $C_1$–$C_{20}$alkyl.

Those intermediates are subject to the preferences indicated for the end product in corresponding manner.

The present invention relates also to a process for the preparation of the compounds of formula I, which process comprises condensing a terpyridine of formula II

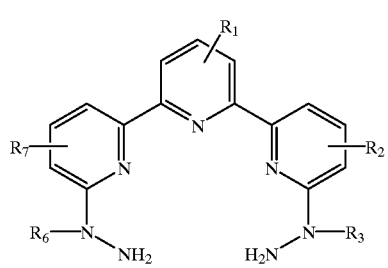

(II)

with a pyridine dialdehyde or pyridine diketone of formula III

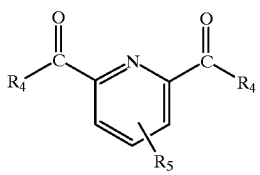

(III)

in the presence of a salt of formula IV

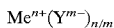  (IV), wherein $R_1$, $R_2$, $R_3$, $R_4$, $R_5$, $R_6$, $R_7$, Me, Y, n and m are as defined above, especially in the definitions, preferences and explanations relating to the compound of formula (I).

The process can be carried out, for example, as follows: the compounds of formulae II, III and IV, preferably in equivalent amounts, are dissolved in a solvent and then reacted with one another at elevated temperatures. It is advantageous also to use condensation catalysts, for example concentrated mineral acids, especially hydrochloric acid, or acidic ion exchangers. It may be advantageous to add water-binding agents or to remove the water of reaction from the reaction mixture.

The reaction temperature may be, for example, from 40 to 220° C., preferably from 50 to 150° C.

The solvents used are advantageously organic polar aprotic solvents. Suitable solvents are, for example, water and polar aprotic solvents which are advantageously water-miscible. Examples of such solvents are alcohols (methanol, ethanol, n- or iso-propanol, butanol, ethylene glycol, propylene glycol, ethylene glycol monomethyl ether, diethylene glycol, diethylene glycol monomethyl ether), ethers (diethyl ether, dibutyl ether, tetrahydrofuran, dioxane, ethylene glycol dimethyl ether, ethylene glycol diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane, chlorobenzene), carboxylic acid esters and lactones (ethyl acetate, propionic acid methyl ester, benzoic acid ethyl ester, 2-methoxyethyl acetate, γ-butyrolactone, δ-valerolactone, pivalolactone), N-alkylated carboxylic acid amides and lactams (N,N-dimethylformamide, N,N-diethylformamide, N,N-dimethylacetamide, tetramethylurea, hexamethylphosphoric acid triamide, N-methyl-γ-butyrolactam, N-methyl-ε-caprolactam, N-methylpyrrolidone), sulfoxides (dimethyl sulfoxide, tetramethylene sulfoxide), sulfones (dimethyl sulfone, diethyl sulfone, trimethylene sulfone, tetramethylene sulfone), tertiary amines (trimethylamine, triethylamine, N-methylpiperidine, N-methylmorpholine, pyridine), substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile).

The metal salts of formula IV are generally known and most are commercially available.

The preparation of the novel compounds of formula II containing a functional group can be carried out analogously to the procedure described by E. C. Constable in Polyhedron, Volume 7, No. 24, pages 2531 to 2536 (1988), functional groups optionally being provided with protecting groups.

Most of the compounds of formulae II and III with or without functional groups are known or they can be prepared in accordance with known or analogous procedures. Compounds of formula III wherein $R_4$ is H, $R_5$ is $C_2$–$C_{18}$alkylene-$X_5$ and $X_5$ is —C(O)—OR, —C(O)—NHR, —SO$_2$—R or —SO$_2$—NHR, and R is H or $C_1$–$C_6$alkyl, are novel and can be obtained as follows: with palladium catalysis a corresponding 3-halo-pyridine-1,5-dicarboxylic acid ester is alkenylated with an alkene of the formula CH$_2$=CH—$C_1$–$C_{16}$alkylene-carboxylic acid ester, the alkene group is hydrogenated, for example catalytically, then reduction to the corresponding 1,5-dihydroxymethylpyridine-alkylcarboxylic acid ester is carried out, and the hydroxymethyl groups are oxidised to aldehyde groups and optionally the ester group is hydrolysed to the carboxylic acid group or the ester group is amidated to the carboxylic acid amide.

Compounds of formula III wherein $R_4$ is $C_1$–$C_{12}$alkyl, $R_5$ is $C_2$–$C_{18}$alkylene-$X_5$ and $X_5$ is —C(O)—OR, —C(O)—NHR, —SO$_2$—R or —SO$_2$—NHR, and R is H or $C_1$–$C_6$alkyl, are novel, and can be obtained as follows: with palladium catalysis a corresponding 3-halo-1,5-dihydroxymethylpyridine protected, for example, by acetyl, (obtainable by reduction of the corresponding 3,5-dicarboxylic acid methyl ester) is alkenylated with an alkene of the formula CH$_2$=CH—$C_1$–$C_{16}$-alkylene-carboxylic acid ester, the alkene group is hydrogenated, for example catalytically, the hydroxyl groups are deprotected and optionally the compound is oxidised to the corresponding 3,5-pyridinealdehyde the aldehyde groups of which can be $C_1$–$C_{12}$alkylated, for example with Grignard reagents, optionally the ester group is hydrolysed to the carboxylic acid group or the ester group is amidated to the carboxylic acid amide, and the secondary alcohol groups are oxidised to keto groups.

The invention relates also to a process for the preparation of compounds of formula V, wherein a compound of formula I is reacted (a) with a compound of formula VIa

  (VIa)

wherein

A" is a suitable monovalent functional group selected from the group consisting of —OR$_{10}$, —SR$_{10}$, —NCO, —NCS, —NHR$_{11}$, —C(O)OR$_{11}$, —C(O)SH, —C(O)NHR$_{11}$, —C(O)Cl, —C(S)SR$_{11}$, —C(S)NHR$_{11}$, —C(S)OR$_{11}$, —SO$_3$R$_{11}$, —SO$_2$NHR$_{11}$, —SO$_2$Cl, —P(O)(OH)$_2$, —P(O)(OH)—NHR$_{11}$, —P(S)(SH)$_2$, —P(S)(SH)—NHR$_{11}$, —P(S)(OH)$_2$, —P(S)(OH)—NHR$_{11}$, —P(O)(SH)$_2$, —P(O)(SH)—NHR$_{11}$, —P(O)(OH)H, —P(O)(NHR$_{11}$)H, —P(S)(SH)H, —P(S)(NHR$_{11}$)H, —P(S)(OH)H and —P(O)(SH)H, with R$_{10}$ being H, —C(O)NH$_2$, —C(S)NH$_2$, —C$_1$–C$_6$alkyl, —C$_x$H$_{2x}$—NH$_2$, —C$_x$H$_{2x}$—SH or —(C$_x$H$_{2x}$O)$_y$—H and x being a number and R$_{11}$ being H, —C$_1$–C$_6$alkyl, —C$_x$H$_{2x}$—NH$_2$, —C$_x$H$_{2x}$—SH or —(C$_x$H$_{2x}$O)$_y$—H and x being a number from 2 to 6 and y being a number from 1 to 20, X' is a radical selected from the group consisting of $C_1$–$C_{20}$alkylene, $C_2$–$C_{12}$alkenylene, $C_2$–$C_{12}$alkynylene, —(C$_x$H$_{2x}$O)$_y$—, wherein x is a number from 2 to 6 and y is a number from 1 to 20, $C_5$–$C_8$cycloalkylene, $C_6$–$C_{12}$arylene and $C_7$–$C_{12}$aralkylene, which radical is unsubstituted or substituted by $C_1$–$C_4$alkoxy, F, Cl, Br, —CN, $C_1$–$C_4$alkyl or by —NO$_2$, A' is —O—, —S—, —S—S—, —NR$_{12}$—CO—NR$_{12}$—, —NR$_{12}$—CS—NR$_{12}$—, —NR$_{12}$—, —$NR_{12}$—C(O)—O—, —C(O)O—, —C(O)S—, —C(O)$NR_{12}$—, —C(S)S—, —C(S)O—, —C(S)$NR_{12}$—, —$SO_2NR_{12}$—, —$SO_2$—, —P(O)(OH)O—, —P(S)(SH)S—, —P(S)(SH)O—, —P(S)(OH)O—, —P(O)(SH)S—, —P(O)(OH)S—, —P(O)(SH)O—, —P(O)(OH)—$NR_{12}$—, —P(S)(SH)—$NR_{12}$—, —P(S)(OH)—$NR_{12}$—, —P(O)(SH)—$NR_{12}$—, —HP(O)O—, —HP(S)S—, —HP(O)$NR_{12}$— or —HP(S)$NR_{12}$—, with $R_{12}$ being H or $C_1$–$C_6$alkyl; and "oligo" denotes a natural, modified or synthetic sequence of natural, modified or synthetic deoxynucleosides or peptide nucleic acid building blocks that is bonded via a nucleic base, an internucleotidic bridge or a sugar and the internal region of which is complementary to a target RNA, or (b) with a compound of formula VIb $$A''\text{—oligo} \tag{VIb}$$

wherein

A" and oligo are as defined in (a).

The process according to the invention for the preparation of the oligonucleotide conjugates can be carried out, for example, by dissolving an optionally functionalised oligonucleotide in a solvent or solvent mixture and then adding the terpyridine-lanthanide complex carrying a suitable functional group and then leaving the reaction mixture to finish reacting, optionally with stirring. The conjugate formed can then be purified and, if desired, isolated in a manner known per se.

The reaction temperature may be, for example, from 0 to 120° C., preferably from 20 to 80° C. The reaction is especially carried out at room temperature.

If the linkage reaction is an esterification, transesterification or amidation reaction, the carboxylic acid groups in question can be activated beforehand in known manner, for example by reaction with carbodiimides and N-hydroxysuccinimide.

The reactants are advantageously used in molar ratios. It is, however, also possible for an excess of the catalyst or of the oligonucleotide to be used.

For purification it is possible to use customary methods, advantageously, for example, dialysis, electrophoresis, and chromatographic procedures, such as high-pressure liquid chromatography (HPLC), reverse HPLC, affinity chromatography, ion exchanger chromatography and gel chromatography.

The optionally functionalised oligonucleotides to be used can be prepared in a manner known per se by means of automated synthesisers which are commercially available. Nucleosides for the synthesis thereof are known, and some are commercially available or they can be prepared according to analogous procedures.

The terpyridine-oligonucleotide conjugates according to the invention are excellently suitable for the cleavage, especially the sequence-specific cleavage, of RNA sequences, it being necessary to use only surprisingly small amounts because of their capacity for catalytic action.

The invention relates also to a method of cleaving the phosphate nucleotide bridge of ribonucleic acids under physiological conditions and under the action of a synthetic terpyridine-lanthanide complex, in which method (a) the target RNA is complexed with an oligonucleotide the internal sequence of which is complementary to the target RNA and to which a terpyridine-lanthanide complex is bonded, and (b) then allowed to react and cleaved.

The method according to the invention can be carried out in vivo by administering the oligonucleotides or in vitro by combining a target RNA and an oligonucleotide to be used according to the invention.

Physiological conditions are familiar to the person skilled in the art and include, for example, carrying out the method in an aqueous medium and in a pH range of from 5 to 9, preferably from 5 to 8 and especially from 5 to 7.5, it being possible for the aqueous medium to contain further inert constituents, for example salts of alkali metals or alkaline earth metals, and especially buffer systems.

The method may be carried out at a temperature of, for example, from 0 to 100° C., preferably from 20 to 50° C. and especially from 30 to 40° C.

In the method according to the invention, the cleavage is carried out with transesterification of the phosphate bridge bond to form a fragment having a 2',3'-cyclic phosphate terminal group and a further fragment having a 5'-hydroxyl terminal group. The cyclic phosphate can then be hydrolysed further.

The terpyridine-oligonucleotide conjugates according to the invention can be used as medicaments. In addition, they have a high degree of stability with respect to degradation by nucleases. Especially surprising is their excellent pairing with complementary nucleic acid strands of the RNA type. In addition, they exhibit unexpectedly high cellular uptake. The oligonucleotides according to the invention are therefore suitable especially for antisense technology, that is to say for inhibiting the expression of undesirable protein products by binding to appropriate complementary nucleotide sequences of mRNA (EP 266 099, WO 87/07300 and WO 89/08146). They can be used in the treatment of infections and diseases for example by blocking the expression of bioactive proteins at the nucleic acid stage (for example oncogenes).

The invention relates also to the oligonucleotides according to the invention for use in a therapeutic method for the treatment of diseases in warm-blooded animals, including human beings, by the inactivation of nucleotide sequences in the body. The dosage on administration to warm-blooded animals of approximately 70 kg body weight may be, for example, from 0.01 to 1000 mg per day. Administration is made preferably in the form of pharmaceutical compositions parenterally, for example intravenously or intraperitoneally. For parenteral administration there are suitable especially aqueous solutions of a water-soluble active ingredient, for example a water-soluble physiologically acceptable salt, or aqueous suspensions of such active ingredients, the solutions or suspensions comprising viscosityincreasing agents, for example sodium carboxymethylcellulose, sorbitol and/or dextran and optionally stabilisers. The active ingredient, optionally together with excipients, may also be in the form of a lyophilisate and can be made into a solution prior to administration by the addition of suitable solvents. The conjugates according to the invention can also be administered by inhalation or in a liposomal form of administration.

The conjugates according to the invention can also be used for diagnostic purposes or as molecular-biological tools as sequence-specific endoribonucleases.

The invention relates also to an aqueous composition and especially a pharmaceutical composition based on an aqueous solution or suspension comprising an effective amount of compounds of formula V alone or together with other active ingredients, water as pharmaceutical carrier, preferably in a significant amount, and optionally excipients.

The pharmacologically effective compounds according to the invention can be used in the form of parenterally administrable compositions or in the form of infusion solutions. Such solutions are preferably isotonic aqueous solutions or suspensions, it being possible, for example in the case of lyophilised compositions that comprise the active ingredient alone or together with a carrier, for example mannitol, for such solutions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions, which may if desired comprise other pharmacologically active substances, for example antibiotics, are prepared in a manner known per se, for example by means of conventional dissolving or lyophilising procedures, and comprise approximately from 0.1% to 90%, especially from approximately 0.5% to approximately 30%, for example from 1% to 5%, active ingredient(s).

The drawings show by way of example the structures of hybrids of an antisense-oligonucleotide and a substrate RNA molecule.

FIG. 1 shows diagrammatically a hybrid of a substrate RNA (line labelled "5'") and an antisense oligonucleotide (line labelled "3'"), to which according to the invention a complex (labelled "Ln") is bonded (so-called conjugate). The numbering indicated relates to the nucleotide building blocks of the substrate RNA, the numbering being such that the nucleotide of the substrate RNA that is complementary to the nucleotide of the antisense oligonucleotide to which the complex is bonded is designated "0". The numbering then continues upwards (+1, +2 etc.) in the 3'-direction and downwards (−1, −2 etc.) in the 5'-direction of the substrate RNA.

Figure 2:
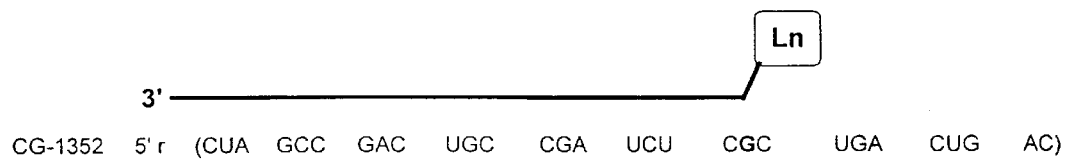

FIG. 2 shows diagrammatically a hybrid of an actual substrate RNA (CG-1352, see Examples) and an antisense oligonucleotide conjugate according to the invention (line labelled "3'"). The nucleotide of the substrate RNA printed in bold type (here: G) is complementary to that nucleotide of the antisense oligonucleotide conjugate to which the complex is bonded.

The following Examples illustrate the invention.

A Preparation of Starting Compounds for the Terpyridine-Lanthanide Complexes

EXAMPLE A1

Preparation of terpyridine-bis-hydrazino compounds (a) With cooling with an ice bath, 40 ml of a 2N aqueous potassium hydroxide solution are added to a solution of 6-acetyl-2-bromopyridine (100 mmol) in 200 ml of methanol. After the addition of the appropriately substituted benzaldehyde (400 mmol) the cooling bath is removed and the mixture is stirred for 4 hours at room temperature. The product is filtered off, washed three times with water and twice with cold methanol and dried under a high vacuum.

In accordance with that procedure, compounds a.1 ($R_1$: phenyl-4-$OCH_3$; MS 317.7), a.2 ($R_1$: phenyl-4-$NO_2$; MS 333.6), a.3 ($R_1$: phenyl-3-$NO_2$, MS 334), a.4 ($R_1$: phenyl-2-$NO_2$, MS 334) and a.5 ($R_1$: phenyl) are prepared.

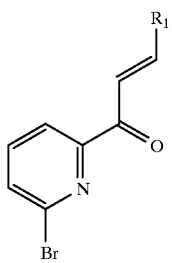

(a)

(b) The α,β-unsaturated carbonyl compound from (a) (30 mmol), 1-(2-bromopyridylcarbonylmethyl)pyridine iodide (12.1 g, 30 mmol) and ammonium acetate (13.9 g, 180 mmol) are placed in a flask, and 100 ml of acetic acid are added thereto. The mixture is boiled at reflux. After 2 hours the mixture is cooled to room temperature and filtered and the product so obtained is dried under a high vacuum.

In accordance with that procedure, compounds b.1 ($R_1$: phenyl-4-$OCH_3$; MS 497.1), b.2 ($R_1$: phenyl-4-$NO_2$; MS 512), b.3 ($R_1$: phenyl-3-$NO_2$, MS 513), b.4 (R.: phenyl-2-$NO_2$, MS 512) and b.5 ($R_1$: phenyl) are prepared.

At room temperature under an argon atmosphere, lithium aluminium hydride (22 mmol) is added in portions to a solution of titanium tetrachloride (30 mmol) in 75 ml of tetrahydrofuran (abs.). The resulting suspension is stirred at room temperature for 20 minutes and then cooled to 0° C. Compound b.2 (10 mmol) is added and the suspension is stirred at room temperature for 30 minutes. After the careful dropwise addition of 50 ml of water at 0° C., 25 ml of a 25% aqueous ammonia solution are added. 150 ml of chloroform are added to the mixture and filtration is carried out over Celite. The aqueous phase is separated off and extracted three times with chloroform. All the organic phases are combined, washed once with water, dried over sodium sulfate and concentrated. In accordance with that procedure, compound b.6 ($R_1$: phenyl-4-$NH_2$; MS 482.5) is prepared. Compounds b.7 ($R_1$: phenyl-3-$NH_2$, MS 482) and b.8 ($R_1$: phenyl-2-$NO_2$, MS 482) are prepared analogously.

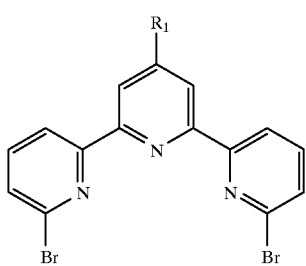

(b)

(c) The appropriate dibromoterpyridine compound from (b) (10 mmol) is dissolved in 30 ml of methylhydrazine and heated under reflux for 17 hours. After cooling to room temperature, the mixture is concentrated and the residue is taken up in 20 ml of methanol. The product is filtered off and dried under a high vacuum.

In accordance with that procedure, compounds c.1 ($R_1$: phenyl-4-$OCH_3$; MS 427), c.2 ($R_1$: phenyl-4-$NH_2$; MS 412.5), c.3 ($R_1$: phenyl-3-$NH_2$, MS 412), c.4 ($R_1$: phenyl-2-$NH_2$, MS 412) and c.5 ($R_1$: phenyl) are prepared.

The methoxy compound c.1 (10 mmol) is suspended in 100 ml of chloroform and, with cooling with an ice bath for 20 minutes, a 1 molar solution of boron tribromide (50 mmol) in methylene chloride is added. The suspension is heated under reflux for 5 days. After cooling to room temperature, the mixture is poured into 300 ml of ice-water, acidified with 200 ml of 2N aqueous hydrochloric acid. After extraction with ether (twice), the aqueous phase is adjusted to pH 9.0 with 10% aqueous sodium carbonate solution and stirred for 30 minutes. The precipitated product c.6 ($R_1$: phenyl-4-OH; MS 413.5) is filtered off and dried under a high vacuum.

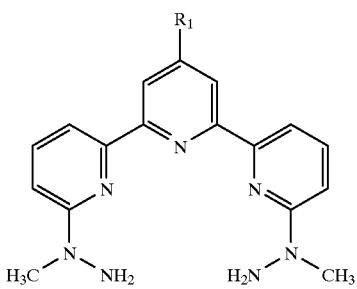

(c)

EXAMPLE A2

Preparation of 3-[4'-(2',6'-diformylpyridine)] propionic acid (a) 3.5 g of 4-bromopyridine-2,6-carboxylic acid dimethyl ester, 390 mg of tritolylphosphine, 9.3 ml of acrylic acid tert-butyl ester, 7.1 ml of triethylamine, 30 ml of dimethylformamide and 287 mg of palladium acetate are mixed and heated at 110° C. After 90 minutes the reaction mixture is cooled to room temperature, diluted with ether/methylene chloride (1:1) and extracted by shaking with $NH_4Cl/H_2O$. The organic phase is dried with $Na_2SO_4$, concentrated using a rotary evaporator and dried under a high vacuum.

|  | C | H | N |
|---|---|---|---|
| calculated | 59.81 | 5.96 | 4.36 |
| found | 59.8 | 6.0 | 4.1 |

250 mg of palladium on active carbon (5%) and 2.5 g of the compound obtained above are dissolved in 250 ml of methanol and hydrogenated overnight at room temperature under an $H_2$ atmosphere. The product is filtered through Hyflo, and the filtrate is concentrated using a rotary evaporator and dried at room temperature under a high vacuum.

|  | C | H | N |
|---|---|---|---|
| calculated | 59.43 | 6.55 | 4.33 |
| found | 59.3 | 6.6 | 4.3 |

5.0 g of the compound obtained above are dissolved in 50 ml of methanol and 50 ml of tetrahydrofuran. After cooling to 0° C., 1.1 g of $NaBH_4$ are added. After 50 minutes a further 1.1 g of $NaBH_4$ are added and after 130 minutes a further 0.5 g of $NaBH_4$ is added. After a total of 165 minutes the reaction mixture is heated to room temperature. The mixture is cooled to 0° C. After 3.5 hours a further 1.1 g of $NaBH_4$ are added. After 6 hours the mixture is concentrated to a volume of 60 ml. A saturated ammonium chloride solution is then added dropwise, extraction is carried out four times with $CH_2Cl_2$, and the organic phases are washed once with ammonium chloride solution, dried with $Na_2SO_4$, filtered and concentrated.

|  | C | H | N |
|---|---|---|---|
| calculated | 62.90 | 7.92 | 5.24 |
| found | 63.0 | 7.9 | 5.2 |

19.8 g of the compound obtained above are dissolved in 300 ml of dioxane. Then 16.2 g of selenium dioxide are added. The reaction mixture is heated at 100° C. and stirred, and after 45 minutes cooled to room temperature. After a further two hours' stirring the reaction mixture is filtered and concentrated using a rotary evaporator.

|  | C | H | N |
|---|---|---|---|
| calculated | 63.87 | 6.51 | 5.32 |
| found | 64.14 | 6.53 | 5.43 |

4.7 g of the compound obtained above are added to 17.2 ml of ice-cold trifluoroacetic acid. After conversion to the acid the mixture is concentrated at 0° C.

|  | C | H | N |
|---|---|---|---|
| calculated | 57.97 | 4.38 | 6.76 |
| found | 57.55 | 4.21 | 6.61 |

(b) 5 g of 4-bromopyridine-2,6-dicarboxylic acid dimethyl ester are dissolved in 175 ml of tetrahydrofuran at room temperature. Then 75 ml of methanol are added. The mixture is cooled to 0° C.; 3.44 g of sodium borohydride are added in portions over a period of 45 minutes and the mixture is allowed to rise to room temperature. After 1 hour 30 ml of acetone are added dropwise within a period of 10 minutes. The reaction mixture is heated under reflux for 1 hour. The reaction mixture is then concentrated to dryness using a rotary evaporator. The residue is stirred at room temperature into 50 ml of pyridine. 0.1 g of 4-dimethylaminopyridine is added thereto and the mixture is then cooled to 0° C. 34.4 ml of acetic anhydride are added dropwise within a period of 30 minutes. The suspension is allowed to rise to room temperature. 50 ml of tetrahydrofuran are added. After being stirred overnight at room temperature, the reaction mixture is filtered and washed twice using 50 ml of tetrahydrofuran each time. The filtrate is concentrated using a rotary evaporator. 4-Bromo-2,6-di(acetoxymethyl)pyridine is obtained by crystallisation (melting point: 66–69° C.).

0.982 g of 4-bromo-2,6-di(acetoxymethyl)pyridine, 1.5 g of 3-(tributylstannyl)-acrylic acid ethyl ester and 176 mg of palladium tetrakis(triphenylphosphine) are dissolved in 25 ml of dioxane and heated at 90° C. After 90 minutes the reaction mixture is cooled. The solid product is separated off and recrystallised from hexane/ethyl acetate. MS 321 ($M^+$).

2.74 g of the compound obtained above and 70 mg of Wilkinson's catalyst are dissolved in 150 ml of benzene. 12.2 ml of triethylsilane are added and the solution is heated at reflux. 270 mg of catalyst triethylsilane in excess are added in portions within a period of one hour. The product is purified by chromatography. MS 323.

267 mg of sodium are dissolved in 50 ml of ethanol. 7.2 ml of that solution are added to a solution of 1.845 g of the compound obtained above in 35 ml of ethanol. After being stirred for 2.5 hours at room temperature the reaction mixture is filtered through silica gel and the filtrate is concentrated to dryness. The product is dried overnight under a high vacuum. NMR (CDCl$_3$) δ 7.0 (2H,s), 4.7 (4H,s), 4.1 (2H,q), 2.9 (2H,t), 1.2 (3H,t).

1.27 g of the compound obtained above are dissolved in 30 ml of dioxane. 714 mg of selenium dioxide are added thereto. The reaction mixture is heated and after 2 hours filtered through cotton wadding. The filtrate is concentrated to dryness. The residue is taken up in ethyl acetate/methylene chloride (5%) and filtered over silica gel. $^1$H-NMR (CDCl$_3$) δ 10.1 (2H,s), 8.0 (2H,s), 4.1 (2H,q), 3.1 (2H,t), 2.7 (2H,t), 1.2 (3H,t).

13 ml of a previously prepared solution (0.949 g of copper bromide.dimethyl sulfide in 10 ml of ether, cooled to 0° C., 5.9 ml of methyllithium added) are added at 0° C. to a solution of 45 ml of ether and 350 mg of the compound obtained above. After being stirred for 5.5 hours at room temperature the mixture is cooled to 0° C. 2 ml of glacial acetic acid in 8 ml of ether are added and 8 ml of ethanethiol. After stirring overnight at room temperature, 60 ml of water are added and the mixture is extracted by shaking four times with methylene chloride. The organic phase is predried with Na$_2$SO$_4$, filtered, concentrated using a rotary evaporator and purified by chromatography. MS 266 (M+H)$^+$.

0.5 ml of DMSO is added at −78° C. to a solution of 4.5 ml of methylene chloride+oxalyl chloride. After 15 minutes the solution is added to a solution of 193 mg of the compound obtained above in 4 ml of methylene chloride. After two hours at −78° C., 1.5 ml of triethylamine are added. After 30 minutes' stirring at 0° C., 15 ml of water are added and the mixture is extracted by shaking four times with diethyl ether. The organic phase is predried with Na$_2$SO$_4$, concentrated using a rotary evaporator and purified by chromatography.

|  | C | H | N |
|---|---|---|---|
| calculated | 63.87 | 6.51 | 5.32 |
| found | 63.96 | 6.55 | 5.45 |

0.464 g of the compound obtained above and 5 ml of 4N HCl are heated together at 50° C. After 90 minutes the reaction mixture is cooled to room temperature and diluted with ice-water. The crystalline product is obtained.

|  | C | H | N |
|---|---|---|---|
| calculated | 61.27 | 5.57 | 5.95 |
| found | 61.2 | 5.5 | 6.2 |

EXAMPLE A3

Preparation of further terpyridine-bis-hydrazino compounds and 2,6-dicarbonylpyridine compounds 1. Preparation of the 2,6-dicarbonyl compound (f)

(a) Preparation of compound (d):

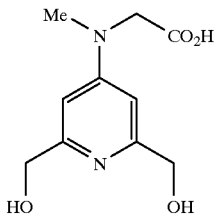

(d)

0.3 g (1.4 mmol) of 2,6-di(hydroxymethyl)-4-bromopyridine, 0.25 g (2.8 mmol) of sarcosine and 0.11 g (2.8 mmol) of NaOH are added to a solution of 15 ml of methanol and 15 ml of water. The operation is carried out under nitrogen at a pressure of 250 bar. The mixture is heated at 100° C. and is allowed to boil until 2,6-di(hydroxymethyl)-4-bromopyridine can no longer be detected. After two days the reaction is complete. The brown reaction mixture is concentrated and the product is purified by chromatography (eluant: 20–80% MeOH/CH$_2$Cl$_2$). A yellow oil is obtained.

$^1$H-NMR (MeOH): δ 6.6 (2H)s; 4.5 (4H)s; 3.8 (2H)s; 3.1 (2H)s; 3.0 (3H)s.

(b) Preparation of compound (e):

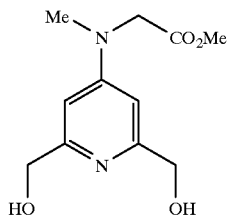

(e)

A suspension of 5.4 g of the crude product (d) obtained as above in 450 ml of methanol is prepared and heated at boiling. 6 ml of concentrated sulfuric acid are added thereto so that a clear solution is obtained. The solution is heated under reflux for 3 hours. The solution is allowed to cool; 5 g of potassium carbonate are added and the mixture is stirred for 10 minutes. Solid is filtered off and the solvent is removed using a rotary evaporator. The crude product is then purified over a column of silica gel (silica gel 44 g; eluant 1:9:50 acetic acid/methanol/methylene chloride). A yellow crystalline solid is obtained.

$^1$H-NMR (MeOD): δ 6.8 (2H)s; 4.6 (4H)s; 3.7 (2H)s; 3.7 (3H)s; 3.2 (3H)s.

(c) Preparation of compound (f):

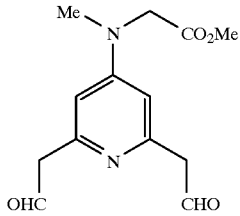

(f)

A solution of compound (e) obtained as above (0.557 g; 2.31 mmol) in 8 ml of pyridine/dioxane (1:1) is heated at boiling. 1.54 g of selenium dioxide (13.7 mmol) are added to the resulting yellow solution and the mixture is heated under reflux for 4 hours (according to TLC starting material is no longer present). The mixture is allowed to cool to room temperature, taken up in ≈100 ml of acetone/methylene chloride (1:9), filtered over a small column of silica gel and washed with the same solvent. The resulting clear yellow solution is concentrated using a rotary evaporator and the crude product is purified by means of column chromatography (eluant: acetone/methylene chloride 1:40). A white solid is obtained.

$^1$H-NMR (CDCl$_3$): δ 10.1 (2H)s; 7.3 (2H)s; 4.2 (2H)s; 3.8 (3H)s; 3.2 (3H)s.

2. Preparation of the 2,6-dicarbonylpyridine compound (k)

(a) Preparation of compound (g):

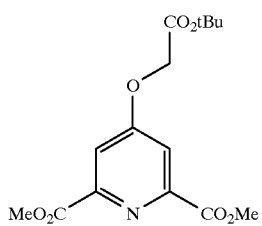

(g)

580 mg of potassium tert-butanolate (5.17 mmol) in 20 ml of dimethyl sulfoxide are placed in a 100 ml sulfonating flask under argon, and 1 g of cheliclamic acid dimethyl ester (4.7 mmol) is added in portions (slightly exothermic reaction). After 10 minutes, 1.04 ml of bromoacetic acid tert-butyl ester (7.05 mmol) in 2 ml of dimethyl sulfoxide are slowly added dropwise to the solution and the mixture is stirred for 3 hours. After being quenched with ice-water the reaction mixture is extracted by shaking three times with 20 ml of diethyl ether. The combined ether phases are counter-washed once with 30 ml of water and then dried with sodium sulfate. The solution is concentrated using a rotary evaporator and dried under a high vacuum. White/yellowish crystals are obtained which are purified over a column of silica gel (70 g of silica gel 60 F, Merck 9385; eluant methanol/dichloromethane 1:100). White crystals are obtained.

$^1$H-NMR (CDCl$_3$): δ 7.8 (2H)s; 4.7 (2H)s; 4.0 (6H)s; 1.5 (9H)s.

(b) Preparation of compound (h):

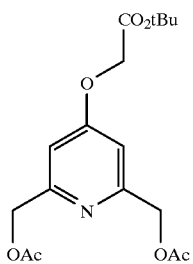

(h)

1.17 g (3.6 mmol) of compound (g) prepared as above are dissolved in 65 ml of dimethoxyethane and cooled to 0° C. 680 mg (18 mmol) of NaBH$_4$ are then added in small portions. The mixture is stirred at 0° C. for 15 minutes. The reaction mixture is then allowed to rise to room temperature. After 3 hours the reaction mixture is cooled to 0° C. again. 12 ml of acetone are added and the mixture is then stirred for 15 minutes. The mixture is heated to room temperature and filtered. The solvent is concentrated using a rotary evaporator and then dried under a high vacuum. The crude product from the first reaction is dissolved in 55 ml of pyridine and cooled to 0° C. 6.8 ml (72 mmol) of acetic anhydride and 44 mg (0.36 mmol) of dimethylaminopyridine are added. The mixture is allowed to rise to room temperature, then diluted with water and extracted by shaking three times with diethyl ether. The organic phases are dried with Na$_2$SO$_4$ and concentrated using a rotary evaporator, then dried under a high vacuum. A brown oil remains behind. The product is purified by means of column chromatography (100 g of silica gel; eluant: 1% methanol in CH$_2$Cl$_2$). The pure product is obtained.

$^1$H-NMR (CDCl$_3$): δ 6.8 (2H)s; 5.2 (4H)s; 4.6 (2H)s.

(c) Preparation of compound (i):

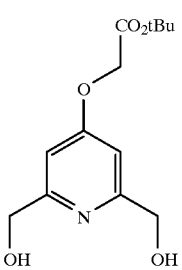

(i)

170 mg (0.48 mmol) of starting material (h) obtained as above are dissolved in 6.5 ml of methanol and cooled to 0° C. 1.7 ml of 32% ammonia solution are added and the mixture is stirred for 1.5 hours. The reaction mixture is concentrated using a rotary evaporator and dried under a high vacuum. A yellow gel is obtained which is purified by means of column chromatography (20 g of silica gel 60 F, Merck No. 9385; eluant methanol/dichloromethane 1:15). A white solid is obtained as end product.

$^1$H-NMR (CD$_3$OD): δ 7.0 (2H)s; 4.8 (2H)s; 4.5 (4H)s; 1.5 (9H)s.

(d) Preparation of compound (j):

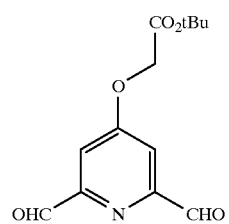

(j)

In a 25 ml taper-necked flask, 260 μl of oxalyl chloride (3.0 mmol) are dissolved in 6 ml of dichloromethane under argon and cooled to –78° C. Then 370 μl of dimethyl sulfoxide (5.25 mmol) are added. The reaction mixture is stirred at –78° C. for 15 minutes. A solution of compound (i) obtained as above (200 mg; 0.75 mmol) in 2 ml of dichloromethane/200 μl of dimethyl sulfoxide is added (monitor the temperature!). After being stirred at –78° C. for 2 hours, the mixture is quenched with 1.04 ml of triethylamine (2.5 mmol) in 2 ml of dichloromethane. The mixture is stirred at 0° C. for a further 15 minutes. The reaction mixture is concentrated using a rotary evaporator and dried under a high vacuum. Brown crystals are obtained which are filtered by means of silica gel 60 F (solvent: hexane:ethyl acetate 2:1).

¹H-NMR (CDCl₃): δ 10.1 (2H)s; 7.6 (2H)s; 4.7 (2H); 1.5 (9H)s.

(e) Preparation of compound (k):

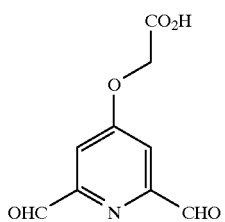

65 mg of compound (j) obtained as above are stirred in 14 ml of 4N hydrochloric acid solution at room temperature for 1.5 hours. The reaction mixture is concentrated to dryness using a rotary evaporator and dried under a high vacuum. Slightly yellowish crystals are obtained as crude product.

¹H-NMR (CD₃OD): δ 7.4 (2H)s; 5.1 (2H)s.

3. Preparation of the terpyridine-bis-hydrazino compound (o)

(a) Preparation of compound (m):

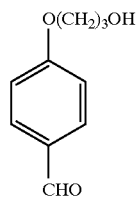

11.49 g (205 mmol) of KOH are pulverised, then placed in a vessel together with 20 g (164 mmol) of 4-hydroxybenzaldehyde and 1.66 g (4.09 mmol) of Aliquat 336. The mixture is stirred using a half-anchor stirring device, cooled in an ice bath, and then 14.24 ml (164 mmol) of 3-bromopropanol are carefully added dropwise. The reaction mixture is heated at 100° C. The dark-brown suspension is stirred overnight at 100° C. under argon. 250 ml of CH₂Cl₂ are added to the reaction mixture and stirring is continued. The resulting suspension is filtered over Hyflo, concentrated, and dried under a high vacuum. The crude product is purified in two portions by chromatography using flash columns (eluant: 2% THF/CH₂Cl₂), yielding the end product.

¹H-NMR (CDCl₃): δ 9.9 (1H)s; 7.8 (2H)d; 7.0 (2H)d; 4.2 (2H)t; 3.9 (2H)m; 2.1 (2H)m; 1.9 (1H)s.

(b) Preparation of compound (n):

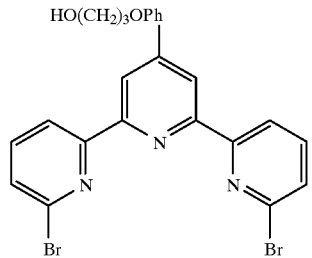

13 g of compound (m) obtained as above (0.072 mol), 28.86 g of 2-acetyl-6-bromopyridine (0.144 mol), 63.72 g of acetamide (1.08 mol) and 41.58 g of ammonium acetate (0.54 mol) are placed in a flask and stirred at 180° C. for 2 hours. The brown suspension is cooled to 120° C. and a solution of 140 g of sodium hydroxide pellets in 300 ml of water is added dropwise thereto. The reaction mixture is boiled for 2 hours. A dark-brown gum is formed which is separated from the supernatant solvent by decanting and washed once more with water. The black gum-like substance is dissolved in as little glacial acetic acid as necessary. An equivalent amount of hydrogen bromide (48% in water) is added to the hot solution and the mixture is left to stand overnight. The light-yellow crystals are filtered off with suction; water is added and the pH is adjusted to a value of 7–8 with 4N potassium hydroxide solution. The yellow suspension is extracted three times with dichloromethane. The organic phase is filtered over cotton wadding, concentrated using a rotary evaporator and dried under a high vacuum. The crude product is recrystallised from ethanol. Yellow crystals are obtained.

MS Peak calculated: 543 m/z (M+H⁺); Peak found: 542 m/z (M+H⁺)

(c) Preparation of compound (o):

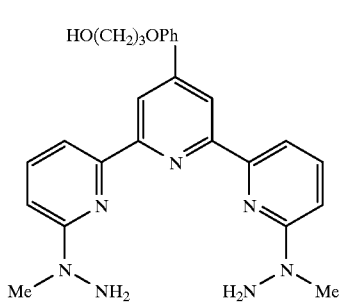

6.38 g of compound (n) obtained as above are placed in 88 ml of methyl hydrazine. The mixture is heated at 85° C. and stirred for 2 hours. After cooling, 150 ml of MeOH are added so that the product precipitates. The suspension is filtered and the crystals obtained are dried.

¹H-NMR (DMSO): δ 8.5 (2H)s; 7.8 (4H)m; 7.7 (2H)t; 7.2 (2H)d; 7.1 (2H)d; 4.6 (2H)t; 4.1 (2H)t; 3.5 (2H)m; 3.3 (6H)s; 1.9 (2H)m.

4. Preparation of the terpyridine-bis-hydrazino compound (q)

(a) Preparation of compound (p):

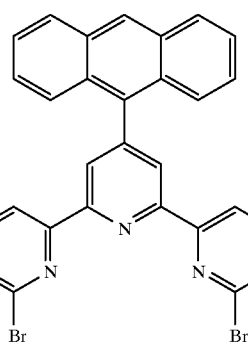

2.6 hg of anthracene-9-carbaldehyde (12.5 mmol), 5 g of 2-acetyl-6-bromopyridine (25 mmol), 11.2 g of acetamide (187.5 mmol) and 7.1 g of ammonium acetate (93.7 mmol) are placed in a flask. The brown solution that forms is heated under reflux for 2 hours (bath temperature 180° C.). After allowing to cool to 110° C., 33 g of sodium hydroxide pellets (0.83 mol) dissolved in 71 ml of water are added dropwise. The reaction mixture is refluxed for a further 2 hours and then cooled to 90° C. The supernatant solution is decanted off and the solid that remains behind is washed twice with water. The black mass is dissolved in 25 ml of acetic acid. 1.75 ml of 48% hydrogen bromide solution are added and the mixture is left to stand for 5 days. The suspension is then filtered and the green precipitate obtained is washed with diethyl ether. The crystals are suspended in water that has been adjusted to a pH value of 8 with 2N potassium hydroxide solution, and extracted by shaking with dichloromethane. After drying of the organic phase with sodium sulfate, concentration using a rotary evaporator and drying in vacuo, a green mass is obtained which is then recrystallised from approximately 400 ml of ethanol. The resulting crystals are taken up in a mixture of ethanol/dichloromethane and extracted by shaking twice with a saturated ammonium carbonate solution. The organic phases are dried over sodium sulfate, concentrated using a rotary evaporator and dried under a high vacuum. The crude product is purified over a column (eluant: hexane:ethyl acetate 9:1). Greenish-brown crystals are obtained.

MS Peak calculated: 568 m/z (M+H⁺); Peak found: 569 m/z (M+H⁺)

(b) Preparation of compound (q):

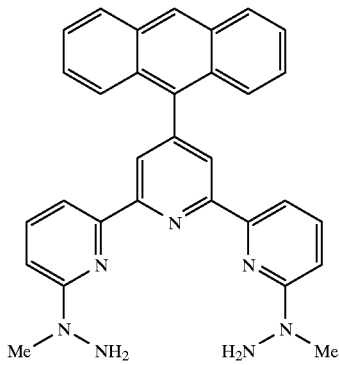

(q)

1.43 g (2.5 mol) of compound (p) obtained as above are added to 50 ml of methyl hydrazine and boiled at reflux overnight. A dark-brown solution is obtained. The solvent is concentrated using a rotary evaporator. The product is suspended in hot methanol and then filtered. 400 mg of green crystals are obtained which are then recrystallised from CH₃CN. The mixture is first filtered until clear, cooled and filtered, then dried under a high vacuum, yielding green crystals. The crystals are again purified by recrystallisation from CH₃CN. Green crystals are again obtained. The mother liquor is likewise concentrated. 1 g of brown crystals is obtained. Those crystals are likewise recrystallised from CH₃CN and then dried under a high vacuum. Light-brown crystals are obtained.

Elementary analysis:

calculated: 74.83% C 5.47% H 19.70% N; found: 74.76% C 5.55% H 19.42% N

5. Preparation of the 2,6-dicarbonyl compound (r):

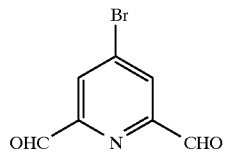

(r)

118 μl (1.38 mmol) of oxalyl chloride are placed in 2 ml of CH₂Cl₂ under argon and cooled to −78° C. 195 μl (2.75 mmol) of DMSO are then carefully added dropwise. The reaction mixture is stirred at −78° C. for 15 minutes. Then 100 mg (0.458 mmol) of 2,6-di(hydroxymethyl)-4-bromopyridine are dissolved in 100 μl of DMSO, and 1 ml of CH₂Cl₂ is added. That solution is added to the reaction mixture. The mixture is stirred at −78° C. for 1 hour. 381 μl (2.75 mmol) of Et₃N are then added and the mixture is stirred at 0° C. for 15 minutes. The mixture is concentrated and dissolved in H₂O and CH₂Cl₂. The two phases are extracted. The aqueous phase is washed twice with CH₂Cl₂. The organic phases are filtered over cotton wadding. Concentration, and drying under a high vacuum yield light-brown crystals.

¹H-NMR (CDCl₃): δ 10.1 (2H)s; 8.7 (2H)s.

6. Preparation of the terpyridine-bis-hydrazino compound (s):

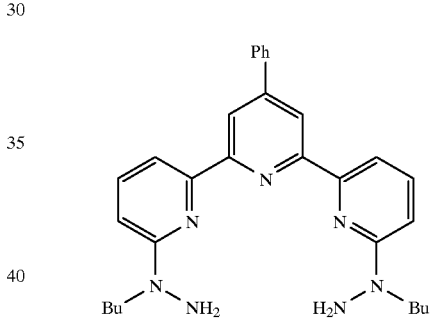

(s)

72 mg of compound b.5 obtained as under Example A1 (b) (0.16 mmol) are taken up in 480 mg of butyl hydrazine (5.44 mmol) and heated at 110° C. under argon. The suspension is boiled overnight. After the reaction mixture has been allowed to cool, it is diluted with diethyl ether and methanol and freed of solid by filtration. The filtrate is concentrated using a rotary evaporator. The addition of methanol causes precipitation. The crystals are filtered off from the refrigerated solution and washed with a small amount of methanol. The product is dried under a slight vacuum. Beige crystals are obtained.

MS Peak calculated: 482 m/z (M+H⁺); Peak found: 481 m/z (M+H⁺)

B Preparation of the terpyridine-lanthanide complexes

EXAMPLE B1

1.) 1 mmol of the respective terpyridine-bis-hydrazino compound from Example A1(c) is taken up in 60 ml of absolute methanol under argon; the lanthanide(III) acetate (1 mmol) is added and the mixture is heated under reflux for 10 minutes. There are then added in succession to that solution 1.2 mmol of the appropriate 2,6-dicarbonyl compound and 5 mmol of concentrated aqueous hydrochloric acid. The mixture is boiled for 2 days. After cooling to room temperature, the product is filtered off and dried under a high vacuum. In accordance with that procedure, compounds 1.1 to 1.28 of Table 1 are prepared.

2.) 1 mmol of the respective terpyridine-bis-hydrazino compound from Example A1(c) is taken up in 60 ml of absolute methanol under argon; the lanthanide(III) chloride (1 mmol) is added and the mixture is heated under reflux for 10 minutes. There are then added in succession to that solution 1.2 mmol of the compound obtained in Example A2(a). The mixture is boiled overnight. After cooling to room temperature, the solvent is removed and the product is obtained by recrystallisation from dimethyl sulfoxide and toluene. In accordance with that procedure, compounds 1.29 to 1.32 of Table 1 are prepared. Compounds 1.33 to 1.44 of Table 1 are obtained analogously.

3.) Preparation of terpyridine-lanthanide complexes with other substituents $R_5$ (a) Preparation of compound 1.45:

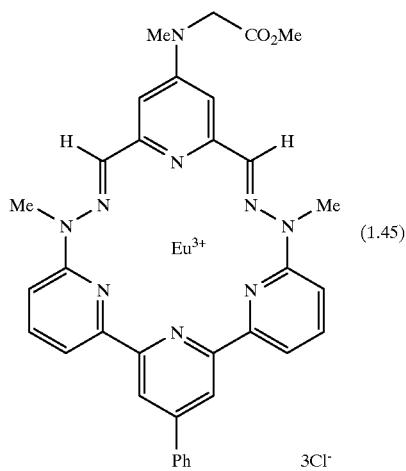

168 mg of compound c.5 obtained as in Example A1(c) (0.423 mmol) are placed in 20 ml of dry methanol and heated at boiling. 155 mg of europium trichloride hexahydrate (0.423 mmol) are then added and the yellow suspension is stirred for 15 minutes. After the addition of 100 mg of compound (f) obtained as in Example A1(c) (0.423 mmol) in 15 ml of dry methanol, the suspension is boiled at reflux overnight under argon. After cooling to room temperature, the reaction mixture is filtered and ⅔ of the solvent is removed from the resulting yellow solution. Orange-coloured crystals are precipitated out of the solution using diethyl ether and filtered off over a millipore filter. The solid is dried under a high vacuum. Orange-coloured crystals are obtained.

MS Peak calculated: 821 m/z (M–Cl⁻); Peak found: 821 m/z (M–Cl⁻)

Compounds 1.46 to 1.58 given in Table 1 are obtained analogously.

(b) Preparation of compound 1.59:

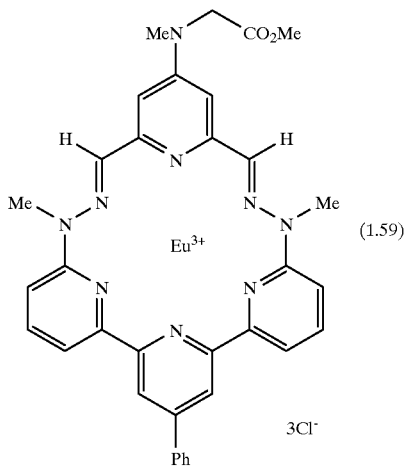

10 mg (0.0116 mmol) of compound 1.45 obtained as above are added to 5 ml of water and heated at reflux. A yellow solution is formed. After three days the reaction mixture is filtered over Acradisk. Concentration, and drying under a high vacuum yield a yellow solid.

4.) Preparation of terpyridine-lanthanide complexes with other substituents $R_5$ (a) Preparation of compound 1.60:

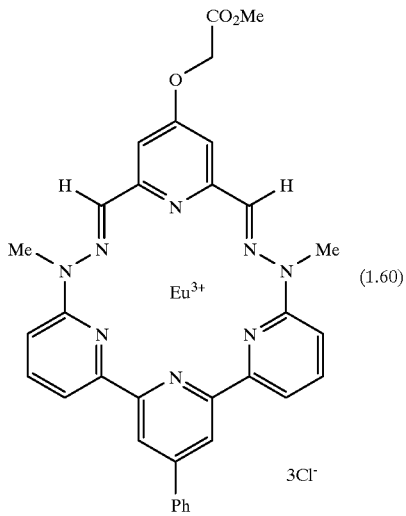

48 mg of compound c.5 obtained as in Example A1 (c) (0.12 mmol) are heated under reflux in 7.5 ml of methanol under argon. 44 mg of europium trichloride hexahydrate (0.12 mmol) are then added and the mixture is boiled under reflux for 15 minutes. After the addition of compound (k) obtained as in Example A3.2(e) in 2.5 ml of methanol, the solution is maintained at boiling for 45 minutes. The cooled suspension is filtered over a filter and the clear yellow solution is concentrated to approximately 2 ml using a rotary evaporator. A yellow precipitate is obtained therefrom using diethyl ether and is then washed once with a solution of diethyl ether/methanol 1:1 and twice with diethyl ether. The residue is dried under a high vacuum. Yellow crystals are obtained.

MS Peak calculated: 807 m/z (M–Cl⁻); Peak found: 809 m/z (M–Cl⁻)

(b) Preparation of compound 1.61:

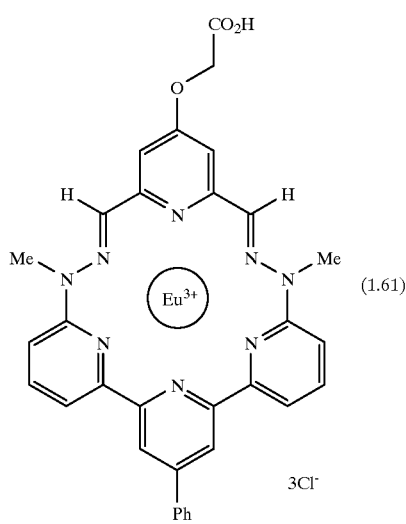

(1.61)

Compound 1.61 is prepared from compound 1.60 analogously to the preparation of compound (1.59) from compound (1.45).

MS Peak calculated: 1056 m/z [M−3Cl⁻+2(C$_8$H$_7$O$_4$)⁻];
Peak found: 1055 m/z [M−3Cl⁻+2(C$_8$H$_7$O$_4$)⁻]

5.) Preparation of terpyridine-lanthanide complexes having other substituents $R_1$ (a) Preparation of compound 1.62:

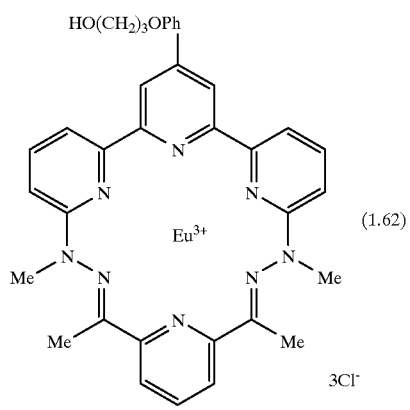

(1.62)

136 mg of compound (o) obtained in Example A3.3(c) (5.94 mmol) are dissolved in 400 ml of dry methanol and heated at reflux under argon. Then 1.53 g of europium trichloride hexahydrate (5.94 mmol) are added and the reaction mixture is boiled at reflux for 0.5 hour. 1 of 2,6-diacetylpyridine (5.94 mmol), which has been dissolved in 100 ml of dry methanol, and 2 drops of concentrated hydrochloric acid are then added to the clear yellow solution that has been formed. The reaction mixture is boiled under reflux for 8 days. After being cooled to room temperature, the suspension is filtered over a Hydro filter. The resulting clear yellow solution is concentrated using a rotary evaporator. A precipitate is produced by means of diethyl ether. The precipitate is washed once with a mixture of diethyl ether/methanol 1:1 and twice with diethyl ether. The residue is dried under a high vacuum. An orange-coloured solid is obtained.

MS Peak calculated: 822 m/z (M−Cl⁻) Peak found: 822 m/z (M−Cl⁻)

6.) Preparation of terpyridine-lanthanide complexes having other substituents $R_5$ (a) Preparation of compound 1.63:

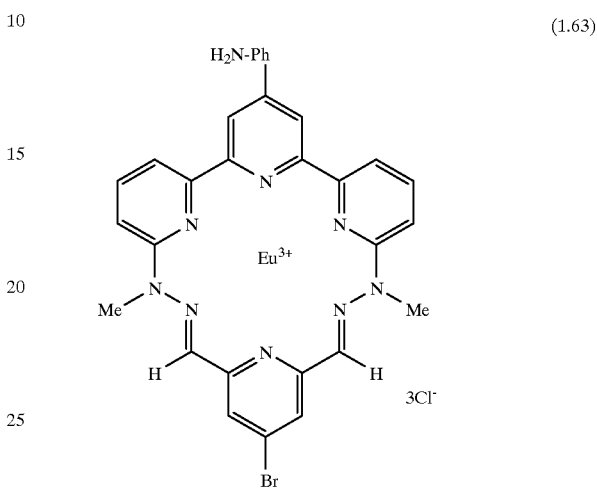

(1.63)

96 mg of compound c.2 obtained as in Example A1 (c) (0.234 mmol) are dissolved in 20 ml of dry methanol and heated at reflux under argon. Then 60 mg of europium trichloride hexahydrate (0.234 mmol) are added and the reaction mixture is boiled at reflux for 0.5 hour. 50 mg of compound (r) obtained as in Example A3.5 (0.234 mmol), which has been dissolved in 15 ml of dry methanol, and 2 drops of concentrated hydrochloric acid are then added to the clear yellow solution that has formed. That reaction mixture is boiled under reflux overnight. After cooling to room temperature, the dark-red suspension is filtered over a Hydro filter. The resulting clear red solution is concentrated using a rotary evaporator and a precipitate is produced by means of diethyl ether. The precipitate is washed once with a mixture of diethyl ether/methanol 1:1 and twice with diethyl ether. The residue is dried under a high vacuum. A dark-red solid is obtained.

MS Peak calculated: 813 m/z (M−Cl⁻) Peak found: 812 m/z (M−Cl⁻)

7. Preparation of terpyridine-lanthanide complexes having other substituents $R_1$ and $R_5$ (a) Preparation of compounds 1.64 to 1.74:

Analogously to the reactions described above, for example analogously to the preparation of compounds 1.62 and 1.63, compounds 1.64 to 1.74 listed in Table 1 are prepared from the correspondingly substituted 2,6-dicarbonylpyridine compounds and the correspondingly substituted terpyridine-bis-hydrazino compounds.

TABLE 1

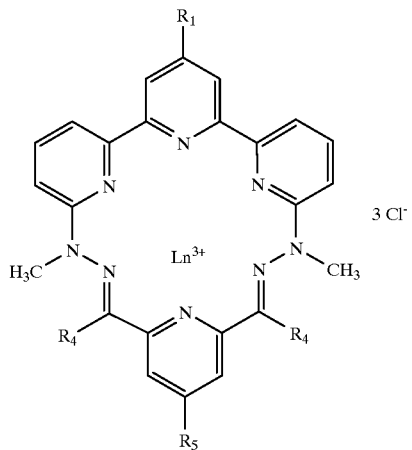

| Comp. No. | $Ln^{3+}$ | $R_1$ | $R_4$ | $R_5$ | molar mass [M—Cl$^-$] calc./found |
|---|---|---|---|---|---|
| 1.1 | La | Ph | H | H | 706/705 |
| 1.2 | La | Ph-4-OH | H | H | 722.4/722.3 |
| 1.3 | La | Ph-4-OCH$_3$ | H | H | 736.4/735.6 |
| 1.4 | La | Ph-4-NH$_2$ | H | H | |
| 1.5 | La | Ph | CH$_3$ | H | 734.4/734.4 |
| 1.6 | La | Ph-4-OH | CH$_3$ | H | 750.4/750.9 |
| 1.7 | La | Ph-4-OCH$_3$ | CH$_3$ | H | 764.5/765.0 |
| 1.8 | La | Ph-4-NH$_2$ | CH$_3$ | H | 749.5/749.5 |
| 1.9 | Eu | Ph | H | H | 719.4/718.9 |
| 1.10 | Eu | Ph-4-OH | H | H | 735.4/735.8 |
| 1.11 | Eu | Ph-4-OCH$_3$ | H | H | 749.5/749.3 |
| 1.12 | Eu | Ph-4-NH$_2$ | H | H | 734.5/734.5 |
| 1.13 | Eu | Ph | CH$_3$ | H | 747.5/747 |
| 1.14 | Eu | Ph-4-OH | CH$_3$ | H | 763.5/763.7 |
| 1.15 | Eu | Ph-4-OCH$_3$ | CH$_3$ | H | 777.5/777.3 |
| 1.16 | Eu | Ph-4-NH$_2$ | CH$_3$ | H | 762.5/762.5 |
| 1.17 | Ce | Ph-4-NH$_2$ | CH$_3$ | H | 750.7/749.3 |
| 1.18 | Pr | Ph-4-NH$_2$ | CH$_3$ | H | 751.4/750.9 |
| 1.19 | Nd | Ph-4-NH$_2$ | CH$_3$ | H | 754.8/752.7 |
| 1.20 | Gd | Ph-4-NH$_2$ | CH$_3$ | H | 767.8/766.3 |
| 1.21 | Tb | Ph-4-NH$_2$ | CH$_3$ | H | 769.5/768.7 |
| 1.22 | Dy | Ph-4-NH$_2$ | CH$_3$ | H | 773.1/773.2 |
| 1.23 | Ho | Ph-4-NH$_2$ | CH$_3$ | H | 775.5/774.4 |
| 1.24 | Er | Ph-4-NH$_2$ | CH$_3$ | H | 777.8/776.8 |
| 1.25 | Tm | Ph-4-NH$_2$ | CH$_3$ | H | 779.5/778.8 |
| 1.26 | Yb | Ph-4-NH$_2$ | CH$_3$ | H | 783.6/783.0 |
| 1.27 | Lu | Ph-4-NH$_2$ | CH$_3$ | H | 785.5/784.7 |
| 1.28 | Y | Ph-4-NH$_2$ | CH$_3$ | H | 699.4/698.1 |
| 1.29 | La | H | H | CH$_2$CH$_2$COOH | |
| 1.30 | Eu | H | H | CH$_2$CH$_2$COOH | |
| 1.31 | La | Ph | H | CH$_2$CH$_2$COOH* | |
| 1.32 | Eu | Ph | H | CH$_2$CH$_2$COOH** | |
| 1.33 | Ce | Ph | H | CH$_2$CH$_2$COOH | 911/912 |
| 1.34 | Pr | Ph | H | CH$_2$CH$_2$COOH | 782/781 |
| 1.35 | Nd | Ph | H | CH$_2$CH$_2$COOH | 915/915 |
| 1.36 | Gd | Ph | H | CH$_2$CH$_2$COOH | 1060/1059 |
| 1.37 | Tb | Ph | H | CH$_2$CH$_2$COOH | 1062/1062 |
| 1.38 | Dy | Ph | H | CH$_2$CH$_2$COOH | 1066/1065 |
| 1.39 | Ho | Ph | H | CH$_2$CH$_2$COOH | 1068/1068 |
| 1.40 | Er | Ph | H | CH$_2$CH$_2$COOH | 1070/1070 |
| 1.41 | Tm | Ph | H | CH$_2$CH$_2$COOH | 905/903 |
| 1.42 | Yb | Ph | H | CH$_2$CH$_2$COOH | 1076/1076 |
| 1.43 | Lu | Ph | H | CH$_2$CH$_2$COOH | 911/908 |
| 1.44 | Y | Ph | H | CH$_2$CH$_2$COOH | 922/922 |
| 1.46 | Ce | Ph | H | N(CH$_3$)CH$_2$C(O)OCH$_3$ | 1071/1071 |
| 1.47 | Pr | Ph | H | N(CH$_3$)CH$_2$C(O)OCH$_3$ | 1072/1071 |
| 1.48 | Nd | Ph | H | N(CH$_3$)CH$_2$C(O)OCH$_3$ | 1075/1073 |
| 1.49 | Gd | Ph | H | N(CH$_3$)CH$_2$C(O)OCH$_3$ | 1089/1091 |
| 1.50 | Tb | Ph | H | N(CH$_3$)CH$_2$C(O)OCH$_3$ | 1091/1092 |
| 1.51 | Dy | Ph | H | N(CH$_3$)CH$_2$C(O)OCH$_3$ | 1094/1094 |
| 1.52 | Ho | Ph | H | N(CH$_3$)CH$_2$C(O)OCH$_3$ | 1097/1097 |
| 1.53 | Er | Ph | H | N(CH$_3$)CH$_2$C(O)OCH$_3$ | 1099/1099 |
| 1.54 | Tm | Ph | H | N(CH$_3$)CH$_2$C(O)OCH$_3$ | 1101/1102 |

TABLE 1-continued

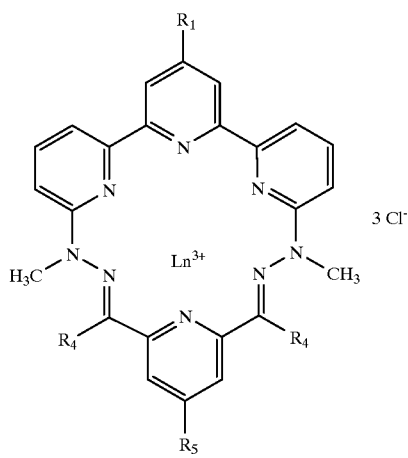

| Comp. No. | Ln$^{3+}$ | R$_1$ | R$_4$ | R$_5$ | molar mass [M—Cl$^-$] calc./found |
|---|---|---|---|---|---|
| 1.55 | Yb | Ph | H | N(CH$_3$)CH$_2$C(O)OCH$_3$ | 1104/1102 |
| 1.56 | Lu | Ph | H | N(CH$_3$)CH$_2$C(O)OCH$_3$ | 1107/1104 |
| 1.57 | Y | Ph | H | N(CH$_3$)CH$_2$C(O)OCH$_3$ | 1020/1020 |
| 1.58 | La | Ph | H | N(CH$_3$)CH$_2$C(O)OCH$_3$ | 1071/1070 |
| 1.64 | Eu | Ph-4-NH$_2$ | Bu | H | 888/888 |
| 1.65 | Eu | Ph-4-NH$_2$ | Ph | H | 847/849 |
| 1.66 | Eu | Ph-4-NH$_2$ | Ph-4-OCH$_3$ | H | 947/948 |
| 1.67 | Eu | Ph-4-NCS | Bu | H | 889/892 |
| 1.68 | Eu | Ph-4-NCS | Ph | H | |
| 1.69 | Eu | Ph-4-NCS | Ph-4-OCH$_3$ | H | 1085/1086*** |
| 1.70 | Eu | 9-anthracenyl | H | CH$_2$CH$_2$C(O)OCH$_3$ | 906/908 |
| 1.71 | Eu | Ph-2-NH$_2$ | CH$_3$ | H | 763/762 |
| 1.72 | Eu | Ph-2-NH$_2$ | CH$_3$ | H | 805/804 |
| 1.73 | Eu | Ph-3-NH$_2$ | CH$_3$ | H | 727/729 |
| 1.74 | Eu | Ph-3-NH$_2$ | CH$_3$ | H | 805/804 |

Ph: phenyl(ene), Bu: butyl

|  | C | H | N | Cl |
|---|---|---|---|---|
| *calc. (+2 DMSO): | 45.81 | 4.16 | 11.55 | 10.96 |
| found: | 45.3 | 4.3 | 11.8 | 10.6 |
| **calc. (+2 DMSO + 4H$_2$O): | 42.11 | 4.58 | 10.62 | 10.07 |
| found: | 42.2 | 4.6 | 10.6 | 9.5 |

***counter-ion is THA*(C$_8$H$_7$O$_4^-$)

EXAMPLE B2

Preparation of Isothiocyanate Derivatives

A solution of the respective complex of Table 1 is added to a suspension of 4.4 mmol of sodium hydrogen carbonate and 3.5 mmol of thiophosgene in 4 ml of chloroform. The mixture is stirred vigorously at room temperature for 2.5 hours. The chloroform phase is separated off and washed once with water. All the aqueous phases are combined and dried. The products 2.1 to 2.15 of Table 2 so obtained are used further without further purification. In analogous manner, from further compounds of Table 1 that contain primary amino groups as substituents there are prepared the corresponding isothiocyanate compounds.

TABLE 2

| Comp. No. | Ln$^{3+}$ | R$_1$ | R$_4$ | R$_5$ | molar mass [M—Cl] calc./found |
|---|---|---|---|---|---|
| 2.1 | Ce | Ph—NCS | CH$_3$ | H | 792.7/792.7 |
| 2.2 | Pr | Ph—NCS | CH$_3$ | H | 793.5/791.2 |
| 2.3 | Gd | Ph—NCS | CH$_3$ | H | 809.9/807.4 |

TABLE 2-continued

| Comp. No. | Ln$^{3+}$ | R$_1$ | R$_4$ | R$_5$ | molar mass [M—Cl] calc./found |
|---|---|---|---|---|---|
| 2.4 | Tb | Ph—NCS | CH$_3$ | H | 811.5/811.7 |
| 2.5 | Dy | Ph—NCS | CH$_3$ | H | 815.1/815.9 |
| 2.6 | Ho | Ph—NCS | CH$_3$ | H | 817.5/816.2 |
| 2.7 | Er | Ph—NCS | CH$_3$ | H | 819.9/819.0 |
| 2.8 | Tm | Ph—NCS | CH$_3$ | H | 821.5/820.1 |
| 2.9 | Yb | Ph—NCS | CH$_3$ | H | 825.6/826.4 |
| 2.10 | Lu | Ph—NCS | CH$_3$ | H | 827.6/825.5 |
| 2.11 | Y | Ph—NCS | CH$_3$ | H | 741.5/740.2 |
| 2.12 | La | Ph—NCS | CH$_3$ | H | 791.5/792.1 |
| 2.13 | Eu | Ph—NCS | CH$_3$ | H | 804.6/804.7 |
| 2.14 | La | Ph—NCS | H | H | |
| 2.15 | Eu | Ph—NCS | H | H | |

C Preparation of the Amino-oligonucleotides

About 30 mg of the 'controled pore glass' (CPG) solid phase are weighed into a Standard Applied Biosystem reaction vessel for a 1.5 μmol synthesis. The CPG solid phase (1) carries the protected 3'-building block (in the Example, dC) of the amino-oligonucleotide to be synthesised.

(1)
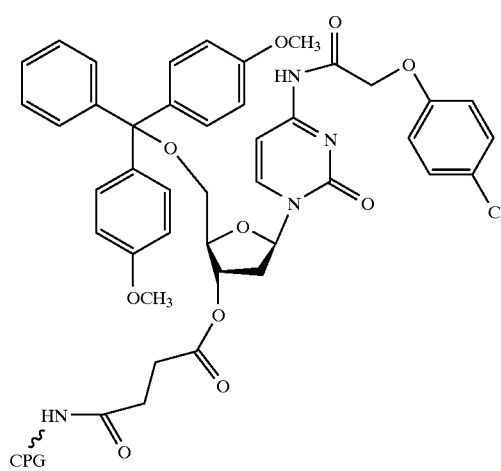
For the oligomerisation, phosphorus amidites (6), (7), (8) and (9) are used.
(6)
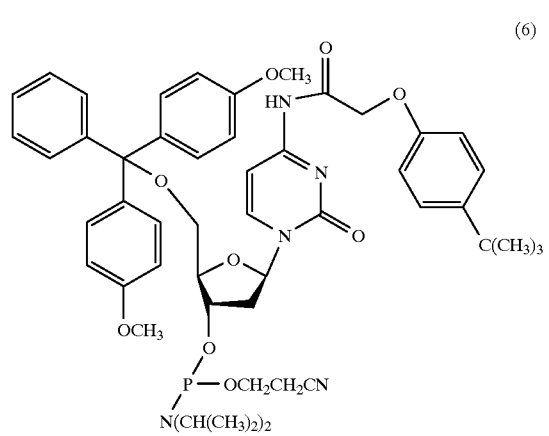
(7)
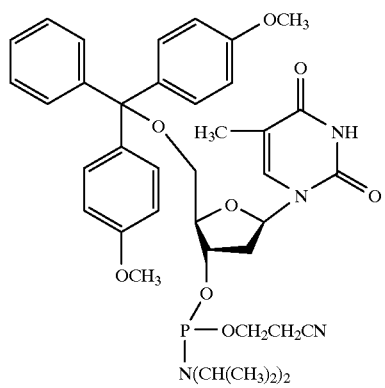
(8)
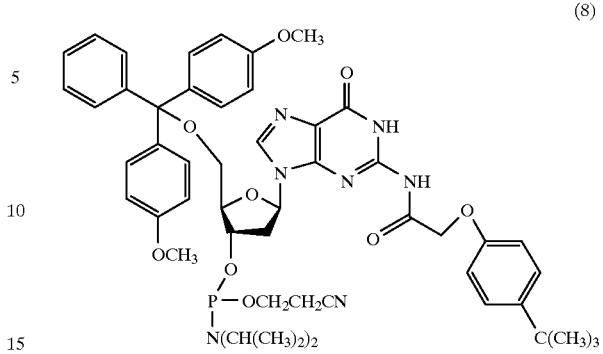
(9)
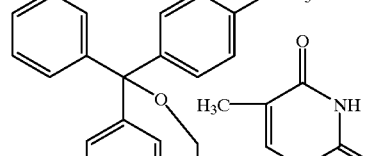
For the later linkage of the metal complexes via the amino function, separate phosphorus amidites (10), (11), (12), (13), (14), (15) and (16) are used.
(10)

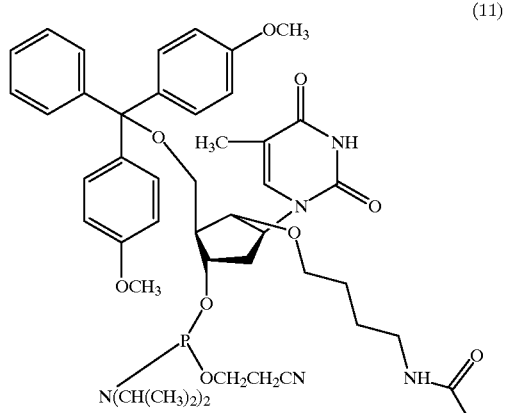

(11)

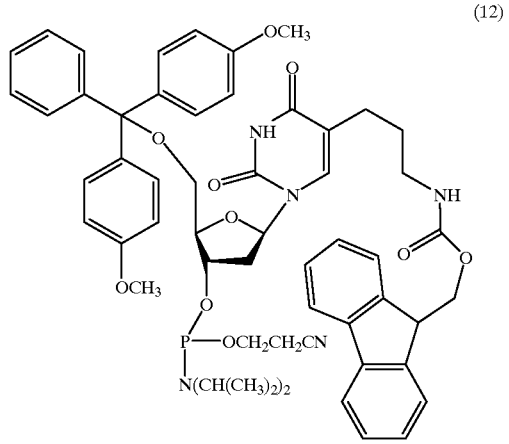

(12)

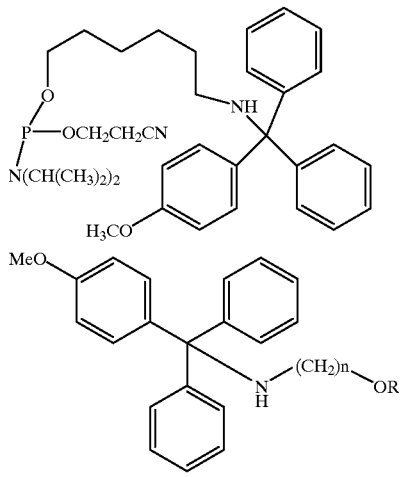

(13)

(14): n = 3, R = P(N(isopropyl)$_2$)OCH$_2$CH$_2$CN
(15): n = 4, R = P(N(isopropyl)$_2$)OCH$_2$CH$_2$CN
(16): n = 5, R = P(N(isopropyl)$_2$)OCH$_2$CH$_2$CN Preparation examples for phosphorus amidites (14), (15) and (16):

Preparation of starting compound (14a) (n=3, R=H):

4.0 g of 3-amino-1-propanol, 3.28 g of 4-methoxytriphenylchloromethane and 35 ml of pyridine are placed in a water-free flask. Stirring is carried out at room temperature and under argon for 4.5 hours. The solvent is concentrated by evaporation. The residue is combined once with toluene and twice with acetonitrile and each time concentrated using a rotary evaporator. The residue is dissolved in methylene chloride and washed twice with saturated sodium hydrogen carbonate solution. The aqueous phases are extracted three times with methylene chloride. The organic phases are combined, dried over sodium sulfate and concentrated. The crude product is then purified by means of flash chromatography (silica gel) (eluant: ethyl acetate/hexane=1:2). A yellow oil is obtained.

$^1$H-NMR: δ in CDCl$_3$, OCH$_3$=3.65.

Starting compounds (15a) (n=4, R=H) and (16a) (n=5, R=H) are prepared analogously from 4-amino-1-butanol and 5-amino-1-pentanol, respectively.

$^1$H-NMR: δ in CDCl$_3$, OCH$_3$=3.65 (15a) and 3.65 (16a).

Preparation of phosphorus amidites (14):

Under argon, 1.99 g of N,N-diisopropylammonium tetrazolide and 3.5 g of 2-cyanoethyl-N,N,N',N'-tetraisopropylphosphorus diamidite are placed in 150 ml of methylene chloride. Within a period of 20 minutes, a solution of compound (14a) obtained as above in 120 ml of methylene chloride is added dropwise thereto. The fine yellow suspension is stirred for 4.5 hours, then diluted with 250 ml of methylene chloride and washed twice with saturated sodium hydrogen carbonate solution. The aqueous phases are extracted three times with methylene chloride. The organic phases are combined, dried over sodium sulfate and concentrated. The crude product is then purified by means of flash chromatography (silica gel) (eluant: ethyl acetate/hexane=1:4+0.5% N-methylmorpholine). A yellow oil is obtained.

$^{31}$P-NMR: δ in CDCl$_3$, 146.9).

Phosphorus amidites (15) and (16) are prepared analogously from compounds (15a) and (16a), respectively, obtained as above.

$^{31}$P-NMR: δ in CDCl$_3$, 146.9 (15) and 147.0 (16).

The synthesis cycles are carried out using the Syntheseautomat 394 by Applied Biosystem with a modification (coupling time of the phosphorus amidites of the deoxy series (6), (7), (8) and (9) is 2 minutes, that of the amidites (10) and (11) is 10 minutes, (12) is 5 minutes and (13) is 40 minutes; (13) is used in 100-fold excess) in accordance with the standard protocol of the Applied Biosystem company (User Manual Version 2.0 (1992) 1.0 μmol cycle, Appendix I-41). For the conjugation of the resulting oligonucleotides with the metal complexes, the respective protecting groups are removed under standard conditions.

Further commercially available reagents used are:

0.1M phosphorus amidite tetrazole/acetonitrile: 4%, 96% tert-butylphenoxyacetic acid anhydride/pyridine/tetrahydrofuran: 10%, 10%, 80%

N-methylimidazole/tetrahydrofuran: 16%, 84% trichloroacetic acid/dimethylchloromethane: 2%, 98% iodine/water/pyridine/tetrahydrofuran: 3%, 2%, 20%, 75%

The following amino-oligonucleotides are synthesised:

(821) 5'-GAC TGG CGA GAT* CGG CAG TCG GCT AG-3', wherein T* is

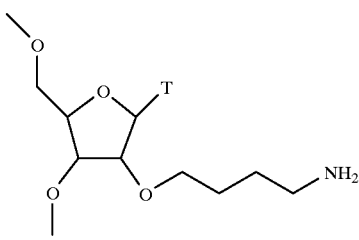

in which T is thymine,
(823) 5'-GAC TGG CGA GAT* CGG CAG TCG GCT AG-3',
wherein T* is

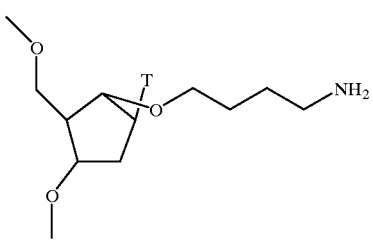

in which T is thymine,
(940) 5'-GAC TGG CGA GAT CGG CAG T*CG GCT AG-3',
wherein T* is

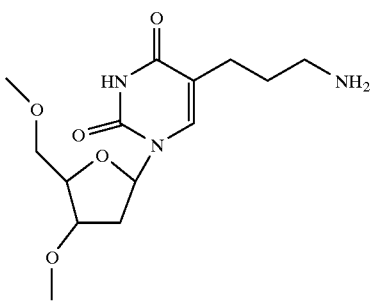

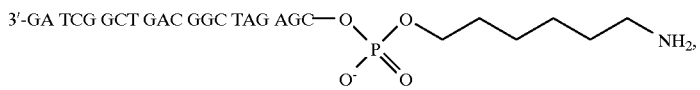

(691)
(1759) 5'-H$_2$N(CH$_2$)$_3$OP(O)$_2$-CGA GAT CGG CAG TCG GCT AG-3',
(1760) 5'-H$_2$N(CH$_2$)$_4$OP(O)$_2$-CGA GAT CGG CAG TCG GCT AG-3',
(1761) 5'-H$_2$N(CH$_2$)$_5$OP(O)$_2$-CGA GAT CGG CAG TCG GCT AG-3', and
(1757) 5'-H$_2$N(CH$_2$)$_6$OP(O)$_2$-GGA GAT CGG CAG TCG GCT AG-3'.

D Preparation of the Terpyridine-lanthanide-oligonucleotide Conjugates

EXAMPLE D1

Preparation of Conjugates in which the Oligonucleotide is Bonded to the Terpyridine Moiety of the Lanthanide Complex (a) 0.2 mg of the respective amino-oligonucleotide is dissolved in 150 μl of pyridine/water/triethylamine (90:15:1). After the addition of 1 mg of the appropriate isothiocyanato complex of Table 2, the mixture is left to stand at room temperature for 1 hour. The reaction mixture is dialysed once against a 0.1 molar potassium chloride solution and three times against water. Purification of the product by reversed-phase HPLC (gradient: from 0% to 30% acetonitrile in 0.05M triethylammonium acetate in 90 minutes) on a Nucleosil®-C$_{18}$-column or by ion exchanger HPLC (gradient: 10 minutes 20% 1M potassium chloride solution and 80% 20 mM potassium phosphate solution pH 6.0 containing 20% acetonitrile; then in the course of 60 minutes to 80% potassium chloride solution) at 60° C. on a PVDI.4000A column, 5 μm, yields the pure conjugates 3.1 to 3.13, 3.18 and 3.21 of Table 3.

(b) 3 mg of the corresponding amino-oligonucleotide are suspended in 200 μl of DMSO/100 μl of N-methyl-morpholine. After the addition of 1 mg of the corresponding isothiocyanate complex (see Table 2 and isothiocyanate complexes prepared analogously from corresponding compounds of Table 1), the mixture is left to stand at room temperature for 2–3 hours. The product is separated from the solid phase by treatment with 32% aqueous ammonia and completely deprotected (3 hours at room temperature). Purification by reversed-phase HPLC yields compounds 3.26 to 3.44 of Table 3.

EXAMPLE D2

Preparation of Conjugates in Which the Oligonucleotide is Bonded to the Pyridine Moiety of the Lanthanide Complex (a) 3.3 μmol of dicyclohexylcarbodiimide and 3.3 μmol of N-hydroxysuccinimide are added to a solution of 3 μmol of the corresponding carboxylic acid derivative 1.29 to 1.32 (Table 1) in 200 μl of dimethyl sulfoxide and the mixture is left to stand at room temperature for 16 hours. After the addition of 100 μmol of N,N-diisopropylethylamine, 0.2 mg of the corresponding amino-oligonucleotide is added. After four days at room temperature, the reaction mixture is dialysed twice against 50 mM triethylammonium hydrogen carbonate and twice against water. Purification by reversed-phase HPLC (see D1(a)) yields compounds 3.14 to 3.17, 3.19, 3.20 and 3.22 to 3.25 of Table 3.

(b) 3.3 μmol of dicyclohexylcarbodiimide and 3.3 μmol of N-hydroxysuccinimide are added to a solution of 3 μmol of the corresponding carboxylic acid derivative (see also Table 1) in 200 μl of dimethyl sulfoxide and the mixture is left to stand at room temperature for 16 hours. After the addition of 3 mg of amino-oligonucleotide, 100 μl of N-methylmorpholine are added. After three days at room temperature, the reaction mixture is washed twice with DMSO and once with water. The product is separated from the solid phase by treatment with 32% aqueous ammonia and completely deprotected (3 hours at room temperature). Purification by reversed-phase HPLC yields compounds 3.45 to 3.49 of Table 3.

TABLE 3

| Comp. No. | Ln | $R_4$ | $R_9$ | $R_8$ | MM (MS) | RT |
|---|---|---|---|---|---|---|
| 3.1 | La | $CH_3$ | Ph-4-691 | H | 7082/7093 | |
| 3.2 | Eu | $CH_3$ | Ph-4-691 | H | 7095/7090 | |
| 3.3 | Ce | $CH_3$ | Ph-4-691 | H | | 27.4 |
| 3.4 | Pr | $CH_3$ | Ph-4-691 | H | | 42.5* |
| 3.5 | Gd | $CH_3$ | Ph-4-691 | H | | 27.0 |
| 3.6 | Tb | $CH_3$ | Ph-4-691 | H | | 27.7 |
| 3.7 | Dy | $CH_3$ | Ph-4-691 | H | | 27.6 |
| 3.8 | Ho | $CH_3$ | Ph-4-691 | H | | 26.7 |
| 3.9 | Er | $CH_3$ | Ph-4-691 | H | | 27.2 |
| 3.10 | Tm | $CH_3$ | Ph-4-691 | H | | 27.5 |
| 3.11 | Yb | $CH_3$ | Ph-4-691 | H | | 28.8 |
| 3.12 | Lu | $CH_3$ | Ph-4-691 | H | | 27.9 |
| 3.13 | Y | $CH_3$ | Ph-4-691 | H | | 27.4 |
| 3.14 | Eu | H | -phenyl | A-691 | 7060/7065 | |
| 3.15 | La | H | -phenyl | A-691 | 7048/7072 | |
| 3.16 | Eu | H | H | A-691 | | |
| 3.17 | La | H | H | A-691 | | |
| 3.18 | Eu | $CH_3$ | Ph-4-821 | H | 9843/9853 | |
| 3.19 | La | H | -phenyl | A-821 | 9800/9800 | |
| 3.20 | Eu | H | -phenyl | A-821 | 9813/9839 | |
| 3.21 | Eu | $CH_3$ | Ph-4-823 | H | 9842/9861 | |
| 3.22 | La | H | -phenyl | A-823 | | 35.6* |
| 3.23 | Eu | H | -phenyl | A-823 | 9811/9826 | |
| 3.24 | La | H | -phenyl | A-940 | 9757/9829 | |
| 3.25 | Eu | H | -phenyl | A-940 | 9770/9794 | |
| 3.26 | Eu | $CH_3$ | Ph-3-691 | H | 7092/7117 | |
| 3.27 | Eu | $CH_3$ | Ph-4-1759 | H | 7050/7043 | |
| 3.28 | Eu | $CH_3$ | Ph-4-1750 | H | 7064/7071 | |
| 3.29 | Eu | $CH_3$ | Ph-4-1761 | H | 7078/7078 | |
| 3.30 | Eu | H | Ph-4-691 | H | 7067/7066 | |
| 3.31 | La | H | Ph-4-691 | H | 7078/7060 | |
| 3.32 | Eu | $CH_3$ | Ph-3-1759 | H | 7053/7058 | |
| 3.33 | Eu | $CH_3$ | Ph-3-1760 | H | 7067/7064 | |
| 3.34 | Eu | $CH_3$ | Ph-3-1761 | H | 7081/7085 | |
| 3.35 | Eu | $CH_3$ | Ph-2-691 | H | 7096/7098 | |
| 3.36 | Eu | $CH_3$ | Ph-2-1759 | H | 7053/7055 | |
| 3.37 | Eu | $CH_3$ | Ph-2-1760 | H | 7067/7065 | |
| 3.38 | Eu | $CH_3$ | Ph-2-1761 | H | 7081/7083 | |
| 3.39 | Eu | H | Ph-4-1759 | H | 7025/7030 | |
| 3.40 | Dy | H | Ph-4-1759 | H | 7036/7043 | |
| 3.41 | Gd | H | Ph-4-1759 | H | 7031/7034 | |
| 3.42 | Dy | H | Ph-3-1759 | H | 7036/7038 | |
| 3.43 | Gd | H | Ph-3-1759 | H | 7031/7029 | |
| 3.44 | Eu | H | Ph-3-1759 | H | 7025/7026 | |
| 3.45 | Eu | H | -phenyl | A-1759 | 7018/7021 | |
| 3.46 | Eu | H | -phenyl | A-1757 | 7100/7123 | |
| 3.47 | Gd | H | -phenyl | A-691 | 7065/7217 | |
| 3.48 | Tb | H | -phenyl | A-691 | 7078/7067 | |
| 3.49 | Eu | H | -phenyl | B-691 | 7075/7097 | |

MM: molar mass calculated/found
RT: ion exchanger HPLC retention time (minutes)
Ph-4-691: -phenyl-4-N(H)C(S)-oligo 691
Ph-4-821: -phenyl-4-N(H)C(S)-oligo 821
Ph-4-823: -phenyl-4-N(H)C(S)-oligo 823
Ph-3-NH-691: -phenyl-3-N(H)C(S)-oligo 691
Ph-2-NH-691: -phenyl-2-N(H)C(S)-oligo 691
Ph-4-1759: -phenyl-4-N(H)C(S)-oligo 1759
Ph-4-1760: -phenyl-4-N(H)C(S)-oligo 1760
Ph-4-1761: -phenyl-4-N(H)C(S)-oligo 1761
Ph-3-1759: -phenyl-3-N(H)C(S)-oligo 1759
Ph-3-1760: -phenyl-3-N(H)C(S)-oligo 1760
Ph-3-1761: -phenyl-3-N(H)C(S)-oligo 1761
Ph-2-1759: -phenyl-2-N(H)C(S)-oligo 1759
Ph-2-1760: -phenyl-2-N(H)C(S)-oligo 1760
Ph-2-1761: -phenyl-2-N(H)C(S)-oligo 1761
A-691: -4-$CH_2CH_2C(O)$-oligo 691
A-821: -4-$CH_2CH_2C(O)$-oligo 821
A-823: -4-$CH_2CH_2C(O)$-oligo 823
A-940: -4-$CH_2CH_2C(O)$-oligo 940
A-1759: -4-$CH_2CH_2C(O)$-oligo 1759
A-1757: -4-$CH_2CH_2C(O)$-oligo 1757
B-691: -4-$N(CH_3)CH_2C(O)$-oligo 691
*reversed-phase HPLC retention time (minutes)

E Preparation of Substrate RNA (target RNA)

EXAMPLE E1

Substrate RNA Synthesis

About 30 mg of the 'controled pore glass' (CPG) solid phase are weighed into a Standard Applied Biosystem reaction vessel for a 1.5 μmol synthesis. The CPG solid phase (1) carries the protected 3'-building block (in the Example, rC) of the RNA to be synthesised.

(1)

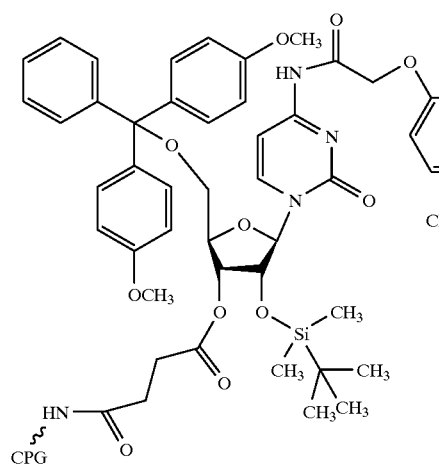

For the oligomerisation, phosphorus amidites (2), (3), (4) and (5) are used.

(2)

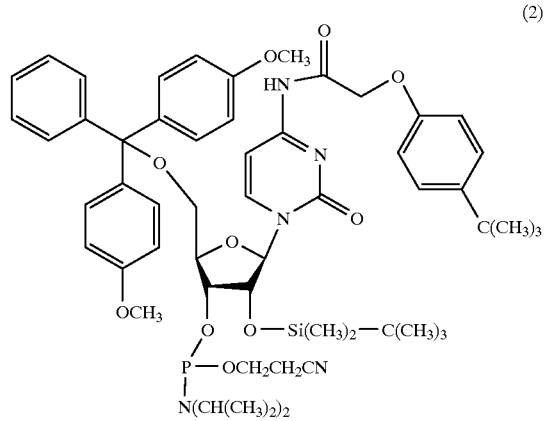

(3)

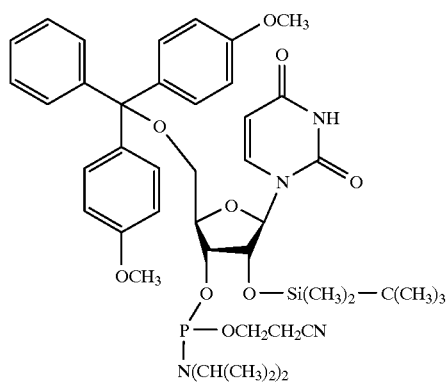

(4)

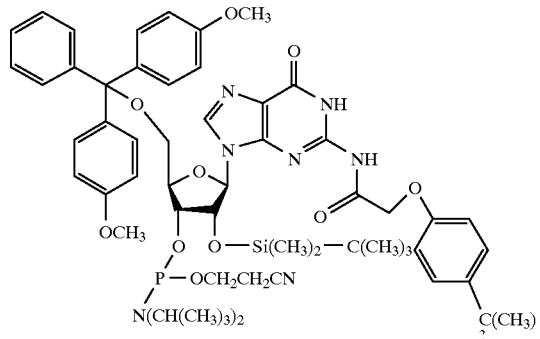

(5)

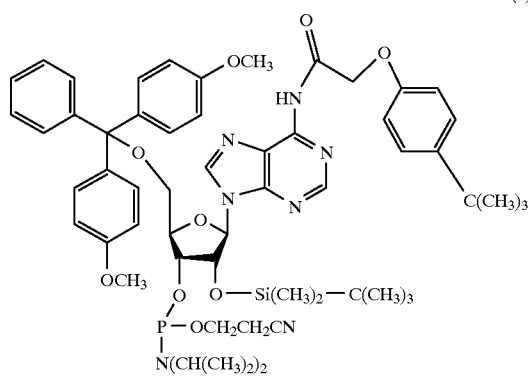

The synthesis cycles are carried out using the Syntheseautomat 394 by Applied Biosystem with a modification (coupling time of the phosphorus amidites of the ribo series is 10 minutes) in accordance with the standard protocol of the Applied Biosystem company (User Manual Version 2.0 (1992) 1.0 μmol cycle, Appendix I-41).

Further commercially available reagents used are:

0.1M phosphorus amidite tetrazole/acetonitrile: 4%, 96% tert-butylphenoxyacetic acid anhydride/pyridine/tetrahydrofuran: 10%, 10%, 80%

N-methylimidazole/tetrahydrofuran: 16%, 84% trichloroacetic acid/dimethylchloromethane: 2%, 98% iodine/water/pyridine/tetrahydrofuran: 3%, 2%, 20%, 75%

The following substrate RNAs are synthesised:

CG-690 5'r(CUA GCC GAC UGC CGA UCU CGC CAC UCU AC)

CG-1352 5'r(CUA GCC GAC UGC CGA UCU CGC UGA CUG AC)

EXAMPLE E2

Separation from the Solid Phase (CPG) and Deprotection of the Base

800 μl of ammonia-saturated ethanol are added to the solid phase (1.5 μmol synthesis) and incubated at room temperature overnight. The ammonia-saturated ethanol is prepared from one part ethanol and three parts 33% ammonia. After the incubation, the ammonia-saturated ethanolic solution is decanted off, the CPG is washed with ammoniacal ethanol and the combined solutions are lyophilised.

EXAMPLE E3

Deprotection of the Tert-butyl-dimethylsilyl (TBDMS) Protecting Group

800 μl of 1M tetrabutylammonium fluoride/tetrahydrofuran (TBAF/THF) solution are added to the lyophilised sample. The sample is mixed intensively for 30 minutes. Incubation is carried out for 24 hours at room temperature with the exclusion of light. The RNA is mixed with 50 mM triethylamine hydrogen carbonate (TAHC) solution pH 7.0 (1+1) and dialysed directly at 4° C. (water has Nanopure® quality).

EXAMPLE E4

Dialysis

Dialysis is carried out 3 times against 7.5 mM TAHC solution pH 7.0. (The solution is prepared using Nanopure® quality water, adjusted to pH 7.0 with $CO_2$ and precooled to 4° C.) The sample is lyophilised and taken up in diethyl-pyrocarbonate-treated [Sambrook, Fritsch, Maniatis, Molecular Cloning, A Laboratory Manual, Second Edition, Cold Spring Harbor Laboratory Press (1989)] and autoclaved $H_2O$ (DEPC-$H_2O$). An aliquot is used for determining the concentration at 260 nm. Further procedures with RNA are always carried out under RNase-free and foreign-metal-ion-free conditions.

EXAMPLE E5

5'-Terminal Labelling of the Substrate RNA with $^{33}$[P]γ-ATP

For the enzymatic kinase reaction, 100 μmol of RNA from the above synthesis protocol are incubated in a volume of 20 μl at 37° C. for 20 minutes. The reaction solution contains 0.5 μl of T4-polynucleotide kinase (Promega, 10 units/μl), 2 μl of kinase buffer (50 mM Tris-HCl pH 7.5, 1 mM $MgCl_2$, 5 mM 1,4-dithio-DL-threitol, 0.1 mM spermidine) and 0.5 μl of $^{33}$[P]γ-ATP (Amersham, >1000 Ci/mmol, 10 μCi/μl). 138 μl of Tris-HCl/EDTA (10 mM/1 mM, pH 7.5), 2 μl of glycogen (35 mg/ml) and 40 μl of $NH_4CH_3COO$ (10M) are then added. After the addition of 600 μl of ethanol, the sample is cooled for 30 minutes at −20° C. and then centrifuged for 20 minutes at 4° C. The pellet is lyophilised; 15 μl of application buffer (0.025% bromophenol blue, 0.025% xylene cylanol in a 1:1 mixture of 80% formamide and 7M urea, 20 mM citric acid, 1 mM EDTA) are added and the mixture is denatured for 1 minute at a temperature of 95° C., immediately placed on ice and for the purpose of gel-electrophoretic separation placed into a 1.0 cm×1 mm bag. The gel-electrophoretic separation is carried out for 2.5 hours at 55 Watt after a pre-run of 40 minutes at 55 Watt.

EXAMPLE E6

Purification and Isolation of the Kinased Substrate RNA

For the gel-electrophoretic separation of the kinase reaction, a 12% polyacrylamide gel (1 mm×30 cm×40 cm) is prepared. The polymerisation reaction is carried out in 170 ml. For that purpose, 51 ml of acrylamide solution (40% acrylamide/bisacrylamide 10:1), 17 ml of TBE buffer (0.89M tri(hydroxymethyl)aminomethane, 0.89M boric acid, 0.02M ethylene-diaminetetraacetic acid) and 71.4 g of urea are mixed with the corresponding amount of $H_2O$. The polymerisation is started with 170 μl of ammonium peroxydisulfate solution (25% w/v) and 170 μl of TEMED (N,N,N',N'-tetramethylethylenediamine). The gel can be used after 1 hour. 10-fold diluted TBE buffer is used as elution buffer. After the gel-electrophoretic separation, the kinased RNA is detected by means of an over-laid X-ray film and excised from the gel. In an electro-elution apparatus (Schleicher and Schuell) the RNA is eluted from the piece of gel by the application of 100 V (3.3 V/cm). 10-fold diluted TBE buffer is used as elution buffer. 40 μl of $NaCH_3COO$ (3M pH 5.2) and 1 ml of ethanol are added to the isolated RNA in 360 μl of eluate. The sample is cooled at −20° C. for 20 minutes and then centrifuged at 4° C. for 20 minutes. The pellet is lyophilised and taken up with 30 μl of $H_2O$. The solution is analysed in a scintillation counter in accordance with the Czerenkow protocol and adjusted to 12 000 cpm/μl.

F Cleavage Experiments with Terpyridine-lanthanide-oligonucleotide Conjugates

EXAMPLE F1

Substrate RNA Cleavage with Oligonucleotide-lanthanide Complex Conjugates

For the gel-electrophoretic separation and identification of the RNA products after the cleavage reaction, a 12% Long Ranger® gel (AT Biochem., modified polyacrylamide gel) (0.4 mm×30 cm×40 cm) is prepared. The polymerisation reaction is carried out in 90 ml. For that purpose, 21 ml of Long Ranger® solution (50%), 11 ml of TBE buffer (0.89M tri-(hydroxymethyl)aminomethane, 0.89M boric acid, 0.02M ethylenediaminetetraacetic acid) and 37 g of urea are mixed with the corresponding amount of $H_2O$. The polymerisation is started with 450 μl of ammonium peroxydisulfate solution (10% w/v) and 45 μl of TEMED. The gel can be used after 1 hour. 16.66-fold diluted TBE buffer is used as elution buffer. The separation takes place within a period of 75 minutes at 60 Watt. After the gel-electrophoretic separation, the labelled cleavage products (RNA oligomers) are detected or counted by means of an overlaid X-ray film or by means of a Phosphorimager®.

The cleavage reaction is carried out in a volume of 10 μl. 1 μl of oligonucleotide conjugate (10 μM), 4 μl of Tris-HCl buffer (50 mM pH 7.4 at 37° C.) and the corresponding amount of $H_2O$ are pipetted into 1 μl of substrate RNA (12 000 cpm). The mixture is heated at 85° C. for 1 minute and then incubated at 37° C. for 16 hours. The reaction is stopped by the addition of 5 μl of application buffer (0.025% bromophenol blue, 0.025% xylene cylanol in a 1:1 mixture of 80% formamide with 7M urea, 20 mM citric acid and 1 mM EDTA). For the gel-electrophoretic separation, 7.5 μl of the sample are denatured for 1 minute at 95° C., immediately placed on ice and placed into a gel bag.

The substrate RNA concentration is estimated as a 25-fold excess as follows: With 100 pmol of crude product of RNA and a yield of 10% in the gel purification, in accordance with the protocol described the final concentrations are 0.04 mM of substrate RNA and 1 mM of oligonucleotide conjugate in the reaction mixture. If the terpyridine-lanthanide complex alone is used as comparison, 400 mM of complex are required in order to achieve approximately the same cleavage. That is a 10 000-fold excess of complex with respect to substrate RNA.

EXAMPLE F2

Incubation of Substrate RNA CG-690 with Oligonucleotide-europium Complex Conjugate Compound No. 3.2

The cleavage reaction takes place in principle as described in Example F1.

(80% starting material uncleaved)
CG-690 5'r(CUA GCC GAC UGC CGA UCU CGC CAC UCU AC)
Main cleavage products
(Σ15%)
5'r(CUA GCC GAC UGC CGA UCU CGC CAC UCU Acp
5'r(CUA GCC GAC UGC CGA UCU CGC CAC UCUcp
5'r(CUA GCC GAC UGC CGA UCU CGC Ccp
5'r(CUA GCC GAC UGC CGA UCU CGcp
Further cleavage products
(Σ5%)
5'r(CUA GCC GAC UGC CGA UCU CGCcp
5'r(CUA GCC GAC UGC CGA UCU Ccp

EXAMPLE F3

Incubation of Substrate RNA CG-690 with Oligonucleotide-lanthanum Complex Conjugate Compound No. 3.15

The cleavage reaction takes place in principle as described in Example F1.

(80% starting material uncleaved)
CG-690 5'r(CUA GCC GAC UGC CGA UCU CGC CAC UCU AC)
Main cleavage products
(Σ20%)
5'r(CUA GCC GAC UGC CGA UCU CGC CAC UCUcp
5'r(CUA GCC GAC UGC CGA UCU CGC Ccp
(cp=2',3'-cyclophosphate)

EXAMPLE F4

Incubation of Substrate RNA CG-1352 with Oligonucleotide-europium Complex Conjugate Compound No. 3.14

The cleavage reaction takes place in principle as described in Example F1.

(<5% starting material uncleaved)
CG-1352 5'r(CUA GCC GAC UGC CGA UCU CGC UGA CUG AC)
Main cleavage product (>70%)
5'r(CUA GCC GAC UGC CGA UCU CGC UGcp)
Residual cleavage products
(Σ25%)
5'r(CUA GCC GAC UGC CGA UCU CGC Ucp)
5'r(CUA GCC GAC UGC CGA UCU CGC UGAcp)
5'r(CUA GCC GAC UGC CGA UCU CGC UGA Ccp)
5'r(CUA GCC GAC UGC CGA UCU CGC UGA CUcp)
5'r(CUA GCC GAC UGC CGA UCU CGC UGACUGcp)

EXAMPLE F5

Further cleavages of substrate RNA CG-1352 with oligonucleotideterpyridine-metal complex conjugates Further cleavage reactions are carried out in principle as described in Example F1. Table 4 shows the results of further cleavages of substrate RNA CG-1352 with various terpyridine-metal complex-oligonucleotide conjugates of Table 3. The figure "+3" indicates that the main cleavage takes place between nucleotides +3 and +4 of the substrate RNA (see also FIG. 1 and FIG. 2 and the associated explanations). It will be seen in the cases shown that the cleavage takes place preferentially at position +3.

TABLE 4

Main cleavage products (positions in bold type) of substrate RNA CG-1352. The conjugate used in each case is indicated (see also Table 3).

| 3.2 | 3.1 | 3.3 | 3.6 | 3.11 | 3.7 |
|---|---|---|---|---|---|
| +3G | +3G | +3G | +3G | +3G | +3G |
| 3.8 | 3.9 | 3.10 | 3.12 | 3.5 | 3.13 |
| +3G | +3G | +3G | +3G | +3G | +3G |
| 3.4 | 3.30 | 3.31 | 3.26 | 3.27 | 3.28 |
| +3G | +3G | +3G | +3G | +3G | +3G |
| 3.29 | 3.32 | 3.33 | 3.34 | 3.35 | 3.36 |
| +3G | +3G | +3G | +3G | +3G | +3G |
| 3.37 | 3.38 | 3.39 | 3.40 | 3.41 | 3.44 |
| +3G | +3G | +3G | +3G | +3G | +3G |
| 3.42 | 3.43 | 3.15 | 3.48 | 3.49 | 3.45 |
| +3G | +3G | +3G | +3G | +3G | +3G |

What is claimed is:

1. A compound of formula I

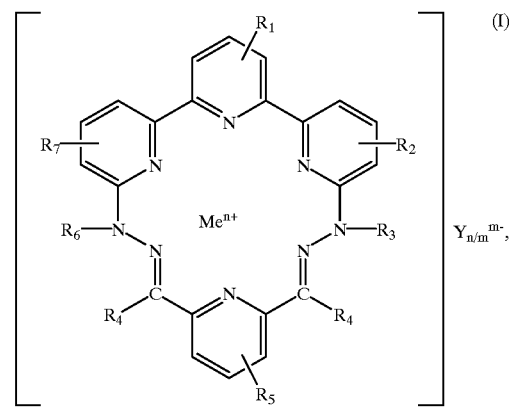

wherein

R$_1$ is H, C$_1$–C$_4$alkyl, C$_1$–C$_4$alkoxy, C$_7$–C$_{12}$aralkyl, C$_6$–C$_{16}$aryl, C$_4$–C$_{12}$heteroaryl having O, S or N as hetero atoms, C$_1$–C$_4$alkylthio, di(C$_1$–C$_4$alkyl)amino, halide, sulfonamide or carboxamide and R$_5$ is a monovalent functional group, or R$_1$ is a monovalent functional group and R$_5$ is H, C$_1$–C$_4$alkyl, C$_1$–C$_4$alkoxy, C$_7$–C$_{12}$aralkyl, C$_6$–C$_{16}$aryl, C$_4$–C$_{12}$heteroaryl having O, S or N as hetero atoms, C$_1$–C$_4$alkylthio, di(C$_1$–C$_4$-alkyl)amino, halide, sulfonamide or carboxamide, the functional group being bonded to the pyridine ring directly or via a group Z and the group Z being a radical selected from the group consisting of C$_1$–C$_{20}$alkylene, C$_2$–C$_{12}$alkenylene, C$_2$–C$_{12}$alkynylene, C$_5$–C$_8$cycloalkylene, C$_6$–C$_{12}$arylene and C$_7$–C$_{12}$aralkylene, which radical is uninterrupted or interrupted by —O—, —S—, —NR$_{12}$—, —C(O)—O— or by —C(O)—NR$_{12}$—, R$_2$ and R$_7$ are each independently of the other H, C$_1$–C$_4$alkyl, C$_1$–C$_4$alkoxy, C$_7$–C$_{12}$aralkyl, C$_6$–C$_{16}$aryl, halogen, C$_4$–C$_{12}$heteroaryl having O, S or N as hetero atoms, C$_1$–C$_4$alkylthio, di(C$_1$–C$_4$alkyl)amino, sulfonamide or carboxamide, R$_3$ and R$_6$ are each independently of the other H, $C_1$–$C_4$alkyl, $C_7$–$C_{12}$aralkyl, $C_6$–$C_{16}$aryl, halogen, $C_4$–$C_{12}$heteroaryl having O, S or N as hetero atoms, $C_1$–$C_4$alkylthio, di($C_1$–$C_4$alkyl)-amino, sulfonamide or carboxamide, $R_4$ is H, $C_1$–$C_{20}$alkyl, $C_5$–$C_8$cycloalkyl, $C_6$–$C_{12}$aryl or $C_7$–$C_{12}$aralkyl, $R_{12}$ is H or $C_1$–$C_6$alkyl, Me is a lanthanide metal or yttrium, Y is an anion of an acid, n is the number 2 or 3, and m is the number 1, 2 or 3, the radicals alkyl, cycloalkyl, aralkyl, aryl and the group Z being unsubstituted or substituted by $C_1$–$C_4$alkoxy, F, Cl, Br, —CN, $C_1$–$C_4$alkyl or by —$NO_2$.

2. A compound according to claim 1, wherein $R_1$ is H, $C_1$–$C_4$alkyl, $C_1$–$C_4$alkoxy, $C_7$–$C_{12}$aralkyl or $C_6$–$C_{16}$aryl, and $R_5$ is a monovalent functional group, or $R_1$ is a monovalent functional group and $R_5$ is H, $C_1$–$C_4$alkyl, $C_1$–$C_4$alkoxy, $C_7$–$C_2$aralkyl or $C_6$–$C_{16}$aryl.

3. A compound according to claim 1, wherein the group Z is $C_1$–$C_3$alkylene, $C_3$alkynylene, phenylene or $C_7$aralkylene.

4. A compound according to claim 1, wherein the group Z is $C_2$–$C_3$alkylene or phenylene.

5. A compound according to claim 1, wherein $R_2$ and $R_7$ are each independently of the other H, $C_1$–$C_4$alkyl, $C_1$–$C_4$alkoxy, $C_7$–$C_{12}$aralkyl, $C_6$–$C_{16}$aryl or halogen.

6. A compound according to claim 1, wherein $R_2$ and $R_7$ are each independently of the other H or $C_1$–$C_4$alkyl.

7. A compound according to claim 1, wherein $R_3$ and $R_6$ are each independently of the other H, $C_1$–$C_4$alkyl, $C_7$–$C_{12}$aralkyl or $C_6$–$C_{16}$aryl.

8. A compound according to claim 1, wherein $R_3$ and $R_6$ are each independently of the other H or $C_1$–$C_4$alkyl.

9. A compound according to claim 1, wherein $R_4$ is H or $C_1$–$C_{20}$alkyl.

10. A compound according to claim 1, wherein the monovalent functional group is selected from the group consisting of —$OR_{10}$, —$SR_{10}$, —NCO, —NCS, —$NHR_{11}$, —C(O)$OR_{11}$, —C(O)SH, —C(O)$NHR_{11}$, —C(O)Cl, —C(S)$SR_{11}$, —C(S)$NHR_{11}$, —C(S)$OR_{11}$, —$SO_3R_{11}$, —$SO_2NHR_{11}$, —$SO_2Cl$, —P(O)(OH)$_2$, —P(O)(OH)—$NHR_{11}$, —P(S)(SH)$_2$, —P(S)(SH)—$NHR_{11}$, —P(S)(OH)$_2$, —P(S)(OH)—$NHR_{11}$, —P(O)(SH)$_2$, —P(O)(SH)—$NHR_{11}$, —P(O)(OH)H, —P(O)($NHR_{11}$)H, —P(S)(SH)H, —P(S)($NHR_{11}$)H, —P(S)(OH)H and —P(O)(SH)H, with $R_{10}$ being H, —C(O)$NH_2$, —C(S)$NH_2$, —$C_1$–$C_6$alkyl, —$C_xH_{2x}$—$NH_2$, —$C_xH_{2x}$—SH or —($C_xH_{2x}$O)$_y$—H, $R_{11}$ being H, —$C_1$–$C_6$alkyl, —$C_xH_{2x}$—$NH_2$, —$C_xH_{2x}$—SH or —($C_xH_{2x}$O)$_y$—H and x being a number from 2 to 6 and y being a number from 1 to 20.

11. A compound according to claim 10, wherein $R_{10}$ is H.

12. A compound according to claim 1, wherein the functional group is selected from the group consisting of —OH, —SH, —NCO, —NCS, —$NHR_{11}$, —C(O)$OR_{11}$ and —P(O)(OH)$_2$.

13. A compound according to claim 1, wherein the functional group is selected from the group consisting of —NCS, —C(O)$OR_{11}$ and —P(O)(OH)$_2$.

14. A compound according to claim 1, wherein the lanthanide metal is La, Ce, Nd, Eu or Gd.

15. A compound according to claim 1, wherein the lanthanide metal is La or Eu.

16. A compound according to claim 1, wherein the lanthanide metal is Eu.

17. A compound according to claim 1, wherein the anion is $F^-$, $Cl^-$, $Br^-$, $I^-$, $PF_6^-$, $SbF_6^-$, $BF_4^-$, $B(Ph)_4^-$, acetate, $NO_3^-$, sulfate or phosphate.

18. A compound according to claim 1, wherein the anion is $Cl^-$, acetate or $NO_3^-$.

19. A compound of formula V

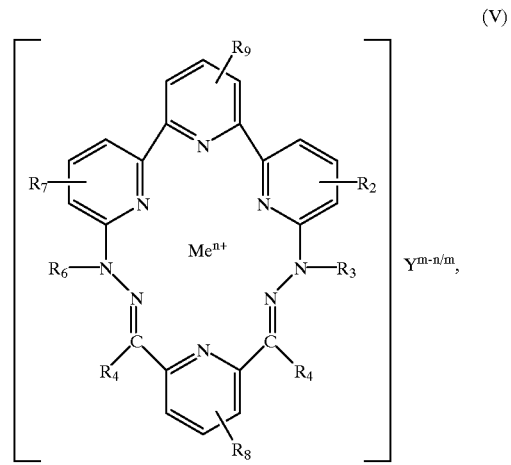

(V)

wherein $R_2$ and $R_7$ are each independently of the other H, $C_1$–$C_4$alkyl, $C_1$–$C_4$alkoxy, $C_7$–$C_{12}$aralkyl, $C_6$–$C_{16}$aryl, halogen, $C_4$–$C_{12}$heteroaryl having O, S or N as hetero atoms, $C_1$–$C_4$alkylthio, di($C_1$–$C_4$alkyl)amino, sulfonamide or carboxamide, $R_3$ and $R_6$ are each independently of the other H, $C_1$–$C_4$alkyl, $C_7$–$C_{12}$aralkyl, $C_6$–$C_{16}$aryl, halogen, $C_4$–$C_{12}$heteroaryl having O, S or N as hetero atoms, $C_1$–$C_4$alkylthio, di($C_1$–$C_4$alkyl)-amino, sulfonamide or carboxamide, $R_4$ is H, $C_1$–$C_{20}$alkyl, $C_5$–$C_8$cycloalkyl, $C_6$–$C_{12}$aryl or $C_7$–$C_{12}$aralkyl, the radicals alkyl, cycloalkyl, aralkyl and aryl being unsubstituted or substituted by $C_1$–$C_4$-alkoxy, F, Cl, Br, —CN, $C_1$–$C_4$alkyl or by —$NO_2$, Me is a lanthanide metal or yttrium, Y is an anion of an acid, n is the number 2 or 3, and m is the number 1, 2 or 3, $R_9$ is a radical of formula VI

—$X_p$—A—$X'_q$—$A'_r$-oligo         (VI), and $R_8$ is H, $C_1$–$C_4$alkyl, $C_1$–$C_4$alkoxy, $C_7$–$C_{12}$aralkyl, $C_6$–$C_{16}$aryl, $C_4$–$C_{12}$heteroaryl having O, S or N as hetero atoms, $C_1$–$C_4$alkylthio, di($C_1$–$C_4$alkyl)amino, halide, sulfonamide or carboxamide, or $R_9$ is H, $C_1$–$C_4$alkyl, $C_1$–$C_4$alkoxy, $C_7$–$C_{12}$aralkyl, $C_6$–$C_{16}$aryl, $C_4$–$C_{12}$heteroaryl having O, S or N as hetero atoms, $C_1$–$C_4$alkylthio, di($C_1$–$C_4$alkyl)amino, halide, sulfonamide or carboxamide and $R_8$ is a radical of formula VI, p, q and r are each independently of the others 0 or 1, X and X' are each independently of the other a radical selected from the group consisting of $C_1$–$C_{20}$alkylene, $C_2$–$C_{12}$alkenylene, $C_2$–$C_{12}$alkynylene, —($C_xH_{2x}$O)$_y$—, wherein x is a number from 2 to 6 and y is a number from 1 to 20, $C_5$–$C_8$cycloalkylene, $C_6$–$C_{12}$arylene and $C_7$–$C_{12}$-aralkylene, which radical is unsubstituted or substituted by $C_1$–$C_4$alkoxy, F, Cl, Br, —CN, $C_1$–$C_4$alkyl or by —$NO_2$, A and A' are each independently of the other —O—, —S—, —S—S—, —$NR_{12}$—CO—$NR_{12}$—, —$NR_{12}$—CS—$NR_{12}$—, —$NR_{12}$—, —$NR_{12}$—C(O)—O—, —C(O)O—, —C(O)S—, —C(O)$NR_{12}$—, —C(S)S—, —C(S)O—, —C(S)$NR_{12}$—, —$SO_2NR_{12}$—, —$SO_2$—, —P(O)(OH)O—, —P(S)(SH)S—, —P(S)(SH)O—, —P(S)(OH)O—, —P(O)(SH)S—, —P(O)(OH)S—, —P(O)(SH)O—, —P(O)(OH)—$NR_{12}$—, —P(S)(SH)—$NR_{12}$—, —P(S)(OH)—$NR_{12}$—, —P(O)(SH)—$NR_{12}$—, —HP(O)O—, —HP(S)S—, —HP(O)$NR_{12}$— or —HP(S)$NR_{12}$—, with $R_{12}$ being H or $C_1$–$C_6$alkyl; and "oligo" denotes a natural, modified or synthetic sequence of natural, modified or synthetic deoxynucleosides or peptide nucleic acid building blocks that is bonded via a nucleic base, an internucleotidic bridge or a sugar and the internal region of which is complementary to a target RNA.

20. A compound according to claim 19, wherein $R_9$ is a radical of formula VI

$-X_p-A-X'_q-A'_r$-oligo  (VI)

and $R_8$ is H, $C_1$–$C_4$alkyl, $C_1$–$C_4$alkoxy, $C_7$–$C_{12}$aralkyl or $C_6$–$C_{16}$aryl, or $R_9$ is H, $C_1$–$C_4$alkyl, $C_1$–$C_4$alkoxy, $C_7$–$C_{12}$aralkyl or $C_6$–$C_{16}$aryl and $R_8$ is a radical of the formula VI, and p, q and r are each independently of the other 0 or 1.

21. A compound according to claim 19, wherein q is 1.
22. A compound according to claim 19, wherein $R_2$ and $R_7$ are each independently of the other H, $C_1$–$C_4$alkyl, $C_1$–$C_4$alkoxy, $C_7$–$C_{12}$aralkyl, $C_6$–$C_{16}$aryl or halogen.
23. A compound according to claim 19, wherein $R_2$ and $R_7$ are each independently of the other H or $C_1$–$C_4$alkyl.
24. A compound according to claim 19, wherein $R_3$ and $R_6$ are each independently of the other H, $C_1$–$C_4$alkyl, $C_7$–$C_{12}$aralkyl or $C_6$–$C_{16}$aryl.
25. A compound according to claim 19, wherein $R_3$ and $R_6$ are each independently of the other H or $C_1$–$C_4$alkyl.
26. A compound according to claim 19, wherein $R_4$ is H or $C_1$–$C_{20}$alkyl.
27. A compound according to claim 19, wherein the lanthanide metal is La, Ce, Nd, Eu or Gd.
28. A compound according to claim 19, wherein the lanthanide metal is La or Eu.
29. A compound according to claim 19, wherein the lanthanide metal is Eu.
30. A compound according to claim 19, wherein the anion is $F^-$, $Cl^-$, $Br^-$, $I^-$, $PF_6^-$, $SbF_6^-$, $BF_4^-$, $B(Ph)_4^-$, acetate, $NO_3^-$, sulfate or phosphate.
31. A compound according to claim 19, wherein the anion is $Cl^-$, acetate or $NO_3^-$.
32. A compound according to claim 19, wherein the anion is $Cl^-$.
33. A compound according to claim 19, wherein X is $C_1$–$C_3$alkylene, $C_3$alkynylene, phenylene or $C_7$aralkylene.
34. A compound according to claim 19, wherein X is $C_2$–$C_3$alkylene or phenylene.
35. A compound according to claim 19, wherein A is —$NR_{12}$—CS—$NR_{12}$— or —C(O)$NR_{12}$—.
36. A compound according to claim 19, wherein A is —NH—CS—NH— or —C(O)NH—.
37. A compound according to claim 19, wherein X' is $C_1$–$C_{20}$alkylene.

38. A compound according to claim 19, wherein X' is $C_1$–$C_{10}$alkylene.
39. A compound according to claim 19, wherein A' is absent or is —P(O)(OH)O—.
40. A method of cleaving a phosphate nucleotide bridge of a ribonucleic acid under physiological conditions using a conjugate of a metal complex and an oligonucleotide, wherein the method comprises the steps of (a) complexing a target RNA with a compound according to claim 19, and (b) cleaving the target RNA.
41. A pharmaceutical composition comprising an aqueous solution or suspension of an effective amount of a compound of formula (V) according to claim 19.
42. A process for the preparation of compounds having the following formula:

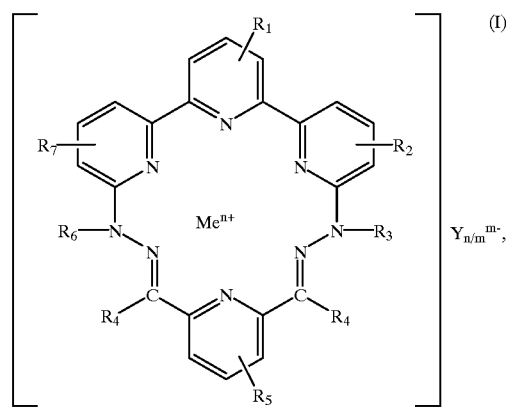

which process comprises condensing a terpyridine of formula II

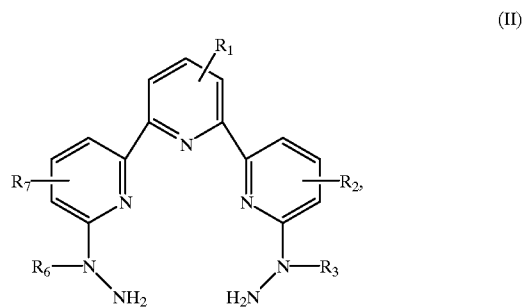

with a pyridine dialdehyde or pyridine diketone of formula III

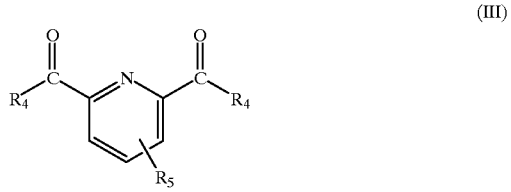

in the presence of a salt of formula IV

$Me^{n+}(Y^{m-})_{n/m}$  (IV), wherein $R_1$ is H, $C_1$–$C_4$alkyl, $C_1$–$C_4$alkoxy, $C_7$–$C_{12}$aralkyl, $C_6$–$C_{16}$ aryl, $C_4$–$C_{12}$heteroaryl having O, S or N as hetero atoms, $C_1$–$C_4$alkylthio, di($C_1$–$C_4$alkyl)amino, halide, sulfonamide or carboxamide and $R_5$ is a monovalent functional group, or $R_1$ is a monovalent functional group and $R_5$ is H, $C_1$–$C_4$alkyl, $C_1$–$C_4$alkoxy, $C_7$–$C_{12}$aralkyl, $C_6$–$C_{16}$aryl, $C_4$–$C_{12}$heteroaryl having O, S or N as hetero atoms, $C_1$–$C_4$alkylthio, di($C_1$–$C_4$alkyl)amino, halide, sulfonamide or carboxamide, the functional group being bonded to the pyridine ring directly or via a group Z and the group Z being a radical selected from the group consisting of $C_1$–$C_{20}$alkylene, $C_2$–$C_{12}$alkenylene, $C_2$–$C_{12}$alkynylene, $C_5$–$C_8$cycloalkylene, $C_6$–$C_{12}$arylene and $C_7$–$C_{12}$aralkylene, which radical is uninterrupted or interrupted by —O—, —S—, —NR$_{,12}$—, —C(O)—O— or by —C(O)—NR$_{12}$—, $R_2$ and $R_7$ are each independently of the other H, $C_1$–$C_4$alkyl, $C_1$–$C_4$alkoxy, $C_7$–$C_{12}$aralkyl, $C_6$–$C_{16}$aryl, halogen, $C_4$–$C_{12}$heteroaryl having O, S or N as hetero atoms, $C_1$–$C_4$alkylthio, di($C_1$–$C_4$alkyl)amino, sulfonamide or carboxamide, $R_3$ and $R_6$ are each independently of the other H, $C_1$–$C_4$alkyl, $C_7$–$C_{12}$aralkyl, or $C_6$–$C_{16}$aryl, $R_4$ is H or $C_1$–$C_{20}$ alkyl, Me is a lanthanide metal or yttrium, Y is an anion of an acid, n is the number 2 or 3, and m is the number 1, 2 or 3.

43. A process for the preparation of compounds having the following formula

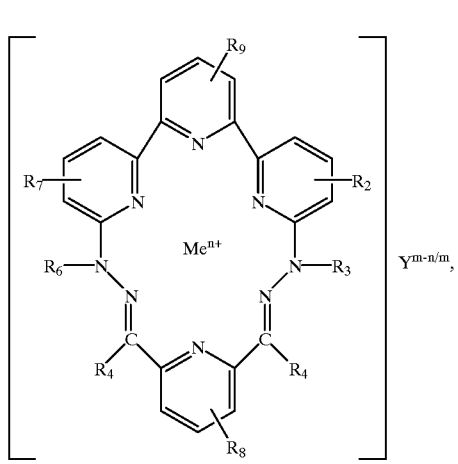

(V)

wherein a compound of formula (I),

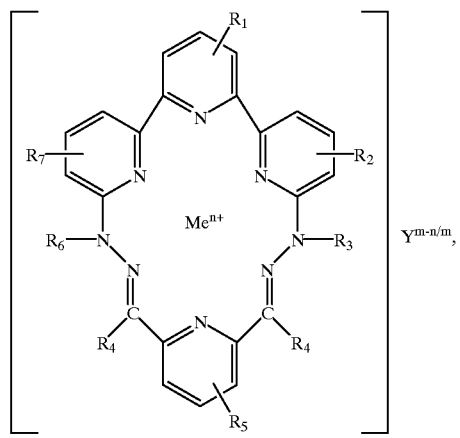

(I)

wherein in formula (I)

$R_1$ is H, $C_1$–$C_4$alkyl, $C_1$–$C_4$alkoxy, $C_7$–$C_{12}$aralkyl, $C_6$–$C_{16}$aryl, $C_4$–$C_{12}$heteroaryl having O, S or N as hetero atoms, $C_1$–$C_4$alkylthio, di($C_1$–$C_4$alkyl)amino, halide, sulfonamide or carboxamide and $R_5$ is a monovalent functional group, or $R_1$ is a monovalent functional group and $R_5$ is H, $C_1$–$C_4$alkyl, $C_1$–$C_4$alkoxy, $C_7$–$C_{12}$aralkyl, $C_6$–$C_{16}$aryl, $C_4$–$C_{12}$heteroaryl having O, S or N as hetero atoms, $C_1$–$C_4$alkylthio, di($C_1$–$C_4$-alkyl)amino, halide, sulfonamide or carboxamide, the functional group being bonded to the pyridine ring directly or via a group Z and the group Z being a radical selected from the group consisting of $C_1$–$C_{20}$alkylene, $C_2$–$C_{12}$alkenylene, $C_2$–$C_{12}$alkynylene, $C_2$–$C_{12}$alkynylene, $C_5$–$C_8$cycloalkylene, $C_6$–$C_{12}$arylene and $C_7$–$C_{12}$aralkylene, which radical is uninterrupted or interrupted by —O—, —S—, —NR$_{12}$—, —C(O)—O— or by —C(O)—NR$_{12}$—, $R_2$ and $R_7$ are each independently of the other H, $C_1$–$C_4$alkyl, $C_1$–$C_4$alkoxy, $C_7$–$C_{12}$aralkyl, $C_6$–$C_{16}$aryl, halogen, $C_4$–$C_{12}$heteroaryl having O, S or N as hetero atoms, $C_1$–$C_4$alkylthio, di($C_1$–$C_4$alkyl)amino, sulfonamide or carboxamide, $R_3$ and $R_6$ are each independently of the other H, $C_1$–$C_4$alkyl, $C_7$–$C_{12}$aralkyl, $C_6$–$C_{16}$aryl, halogen, $C_4$–$C_{12}$heteroaryl having O, S or N as hetero atoms, $C_1$–$C_4$alkylthio, di($C_1$–$C_4$alkyl)-amino, sulfonamide or carboxamide, $R_4$ is H, $C_1$–$C_{20}$alkyl, $C_5$–$C_8$cycloalkyl, $C_6$–$C_{12}$aryl or $C_7$–$C_{12}$aralkyl, $R_{12}$ is H or $C_1$–$C_6$alkyl, Me is a lanthanide metal or yttrium, Y is an anion of an acid, n is the number 2 or 3, and m is the number 1, 2 or 3, the radicals alkyl, cycloalkyl, aralkyl, aryl and the group Z being unsubstituted or substituted by $C_1$–$C_4$alkoxy, F, Cl, Br, —CN, $C_1$–$C_4$-alkyl or by —$NO_2$, is reacted
(a) with a compound of formula VIa

A"—X'A'$_0$ or $_1$-oligo  (VIa)

wherein

A" is a suitable monovalent functional group selected from the group consisting of —$OR_{10}$, —$SR_{10}$, —NCO, —NCS, —$NHR_{11}$, —$C(O)OR_{11}$, —C(O)SH, —C(O)$NHR_{11}$, OC(O)Cl, —$C(S)SR_{11}$, —$C(S)NHR_{11}$, —C(S)$OR_{11}$, —$SO_3R_{11}$, —$SO_2NHR_{11}$, —$SO_2Cl$, —P(O)(OH)$_2$, —P(O)(OH)—$NHR_{11}$, —P(S)(SH)$_2$, —P(S)(SH)—$NHR_{11}$, —P(S)(OH)$_2$, —P(S)(OH)—$NHR_{11}$, —P(O)(SH)$_2$, —P(O)(SH)—$NHR_{11}$, —P(O)(OH)H, —P(O)($NHR_{11}$)H, —P(S)(SH)H, —P(S)($NHR_{11}$)H, —P(S)(OH)H, and —P(O)(SH)H, with $R_{10}$ being H, —C(O)$NH_2$, —C(S)$NH_2$, —$C_1$–$C_6$alkyl, —$C_xH_{2x}$—$NH_2$, —$C_xH_{2x}$—SH or —$(C_xH_{2x}O)_y$—H and $R_{11}$ being H, —$C_1$–$C_6$alkyl, —$C_xH_{2x}$—$NH_2$, —$C_xH_{2x}$—SH or $(C_xH_{2x}O)_y$—H and x being a number from 2 to 6 and y being a number from 1 to 20, X' is a radical selected from the group consisting of $C_1$–$C_{20}$alkylene, $C_2$–$C_{12}$alkenylene, $C_2$–$C_{12}$alkynylene, —$(C_xH_{2xl}\ O_y$—, wherein x is a number from 2 to 6 and y is a number from 1 to 20, $C_5$–$C_8$cycloalkylene, $C_6$–$C_{12}$arylene and $C_7$–$C_{12}$aralkylene, which radical is unsubstituted or substituted by $C_1$–$C_4$alkoxy, F, Cl, Br, —CN, $C_1$–$C_4$alkyl or by —$NO_2$, A' is —O—, —S—, —S—S—, —$NR_{12}$—CO—$NR_{12}$—, —$NR_{12}$—CS—$NR_{12}$—, —$NR_{12}$—, —$NR_{12}$—, —$NR_{12}$—C(O)—O—, —C(O)O—, —C(O)S—, —C(O)$NR_{12}$—, —C(S)S—, —C(S)O, —C(S)$NR_{12}$—, —$SO_2NR_{12}$—, —$SO_2$—, —P(O)(OH)O—, —P(S)(SH)S—, —P(S)(SH)O—, —P(S)(OH)O—, —P(O)(SH)S—, —P(O)(OH)S—, —P(O)(SH)O—, —P(O)(OH)—$NR_{12}$—, —P(S)(SH)$NR_{12}$—, —P(S)(OH)—$NR_{12}$—, —P(O)(SH)—$NR_{12}$—, —HP(O)O, —HP(S)S—, —HP(O)$NR_{12}$— or —HP(S)$NR_{12}$—, with $R_{12}$ being H or $C_1$–$C_6$alkyl; and "oligo" denotes a natural, modified or synthetic sequence of natural, modified or synthetic deoxynucleosides or peptide nucleic acid building blocks that is bonded via a nucleic base, and internucleotidic bridge or a sugar and the internal region of which is complementary to a target RNA, or
(b) with a compound of formula VIb

A"—oligo  (VIb)

wherein

A" and oligo are as defined in (a).

44. A process according to claim 43, wherein $R_{10}$ is H.

* * * * *

UNITED STATES PATENT AND TRADEMARK OFFICE
CERTIFICATE OF CORRECTION

PATENT NO. : 5,925,744
DATED : July 20, 1999
INVENTOR(S) : HÄNER ET AL.

It is certified that error appears in the above-identified patent and that said Letters Patent is hereby corrected as shown below:

At column 2, formula (I), that portion of the formula reading $Y_{n/m}{}^{m\text{-}}$ should read $Y^{m\text{-}}_{n/m}$.

At column 4, formula (V), that portion of the formula reading $Y^{m\text{-}n/m}$ should read $Y^{m\text{-}}_{n/m}$.

At column 10, formula (VIa), that portion of the should read A"-X'-A'$_{0\text{ or }1}$-oligo.

At column 46, formula (I), that portion of the formula reading $Y_{n/m}{}^{m\text{-}}$ should read $Y^{m\text{-}}_{n/m}$.

At column 48, formula (V), that portion of the formula reading $Y^{m\text{-}n/m}$ should read $Y^{m\text{-}}_{n/m}$.

At column 50, formula (I), that portion of the formula reading $Y_{n/m}{}^{m\text{-}}$ should read $Y^{m\text{-}}_{n/m}$.

At column 51, formula (V), that portion of the formula reading $Y^{m\text{-}n/m}$ should read $Y^{m\text{-}}_{n/m}$.

At column 52, formula (I), that portion of the formula reading $Y^{m\text{-}n/m}$ should read $Y^{m\text{-}}_{n/m}$.

At column 53, line 27, the formula reading –$(C_xH_{2xl}\ O)_y$– should read –$(C_xH_{2x}O)_y$–.

Signed and Sealed this
First Day of February, 2000

Attest:

Q. TODD DICKINSON

*Attesting Officer*     *Acting Commissioner of Patents and Trademarks*